United States Patent
Zhu et al.

(10) Patent No.: US 8,357,636 B2
(45) Date of Patent: Jan. 22, 2013

(54) ALKOXYLATED ALKYLAMINES/ALKYL ETHER AMINES WITH PEAKED DISTRIBUTION

(75) Inventors: Shawn Zhu, Stormville, NY (US); Giao Nguyen, Friendswood, TX (US); Kha Nguyen, Seabrook, TX (US); Alberto Slikta, Chicago, IL (US); David Eaton, Kirkwood, MI (US); David Becher, St. Louis, MO (US); Henry Agbaje, St. Louis, MO (US); Michael Seitz, Dublin, CA (US)

(73) Assignee: Akzo Nobel N.V., Arnehm (NL)

( * ) Notice: Subject to any disclaimer, the term of this patent is extended or adjusted under 35 U.S.C. 154(b) by 0 days.

(21) Appl. No.: 13/230,281

(22) Filed: Sep. 12, 2011

(65) Prior Publication Data

US 2012/0053054 A1    Mar. 1, 2012

Related U.S. Application Data

(62) Division of application No. 11/575,847, filed as application No. PCT/US2005/034186 on Sep. 23, 2005, now Pat. No. 8,034,979.

(60) Provisional application No. 60/637,172, filed on Dec. 17, 2004, provisional application No. 60/612,597, filed on Sep. 23, 2004.

(51) Int. Cl.
   *A01N 25/30* (2006.01)

(52) U.S. Cl. ......... 504/358; 504/127; 504/187; 564/505

(58) Field of Classification Search ........................ None
See application file for complete search history.

(56) References Cited

U.S. PATENT DOCUMENTS

| | | | |
|---|---|---|---|
| 4,456,697 A | 6/1984 | Yang | |
| 4,483,941 A | 11/1984 | Yang | |
| 5,012,012 A | 4/1991 | Nakamura et al. | |
| 5,292,910 A | 3/1994 | Raths et al. | |
| 5,389,598 A | 2/1995 | Berk et al. | |
| 5,750,468 A * | 5/1998 | Wright et al. | 504/206 |
| 5,958,835 A | 9/1999 | Baker et al. | |
| 6,235,940 B1 | 5/2001 | Mohr et al. | |
| 6,245,713 B1 | 6/2001 | Brinker et al. | |
| 6,365,551 B1 | 4/2002 | Wright et al. | |
| 6,376,721 B1 | 4/2002 | Priou et al. | |
| 6,770,608 B2 | 8/2004 | Franklin et al. | |
| 7,135,437 B2 | 11/2006 | Pallas et al. | |
| 2002/0016264 A1 | 2/2002 | Shannon et al. | |
| 2002/0065199 A1 | 5/2002 | Wright | |
| 2002/0123430 A1 | 9/2002 | Xu et al. | |
| 2003/0004063 A1 | 1/2003 | Jimoh | |
| 2003/0050194 A1 | 3/2003 | Hopkinson et al. | |
| 2003/0104943 A1 | 6/2003 | Lennon et al. | |
| 2003/0125209 A1 | 7/2003 | Tank | |
| 2004/0063586 A1 | 4/2004 | Kirby et al. | |
| 2004/0198606 A1 | 10/2004 | Mitchell et al. | |
| 2006/0040826 A1 | 2/2006 | Eaton et al. | |
| 2006/0194699 A1 | 8/2006 | Moucharafieh et al. | |
| 2007/0037708 A1 | 2/2007 | Prosch et al. | |
| 2010/0056376 A1 | 3/2010 | Zhu et al. | |

FOREIGN PATENT DOCUMENTS

| | | |
|---|---|---|
| DE | 219478 A1 | 3/1985 |
| EP | 0339426 A2 | 11/1989 |
| EP | 0354993 A2 | 2/1990 |
| EP | 0826715 A1 | 3/1998 |
| JP | 37-4502 | 7/1958 |
| JP | 2003-096186 | 4/2003 |
| WO | 9532272 A1 | 11/1995 |
| WO | 0042847 A1 | 7/2000 |
| WO | 0064257 A1 | 11/2000 |
| WO | 0238269 A1 | 5/2002 |
| WO | 02096199 A2 | 12/2002 |
| WO | 03067983 A1 | 8/2003 |
| WO | 2005104774 A2 | 11/2005 |

OTHER PUBLICATIONS

Hreczuch, W. et al., "Narrow range Distrubuted Ethoxylated Alcohols", Recent Res. Devel. in Oil Chem., (1998), pp. 63-76, vol. 2.
Hreczuch, W. et al., "High Ethoxylated Alcohols with Narrow Distribution of Homologues", Journal of Chemical Technology & Biotechnology, (1996), pp. 53-60, vol. 67.
Akzo Chemie America, "Physical and Chemical Characteristics of Armak Ethoxylated Aliphatic Chemicals", Bulletin 85-10, 1985, 15 pages.
Karsa, D., "Narrow Alcohol Ethoxylates", Design and Selection of Performance, (1999), pp. 146-165, vol. 2, Ch. 4.
English Abstract of EP 0039426; Nov. 2, 1989.
English Abstract of EP 0354993; Feb. 21, 1990.
International Search Report and Written Opinion issued in connection with PCT/US2005/034186, dated Jan. 23, 2006, 13 pages.
International Search Report issued in connection with PCT/US2007/064809, dated Jul. 30, 2008, 7 pages.
English Translation of Japanese Office Action issued in Japanese Patent Application No. 2007-533657, dated Oct. 18, 2011.
English Abstract of JP2003-096186, (2003).

* cited by examiner

*Primary Examiner* — Brian J Davis
(74) *Attorney, Agent, or Firm* — Ralph J. Mancini; Sugiarto Hadikusumo

(57) ABSTRACT

The present invention generally relates to a process for preparing the alkoxylated alkylamines and/or alkyl ether amines. The process consists of three stages, and utilizes an alkali catalyst. The alkoxylated alkyl amines and alkoxylated alkyl ether amines prepared by the process possess the peaked distribution and contain less hazardous by-product.

13 Claims, 7 Drawing Sheets

ALKOXYLATED ALKYLAMINES/ALKYL ETHER AMINES WITH PEAKED DISTRIBUTION

REFERENCE TO RELATED APPLICATIONS

This application is a Divisional application of U.S. Ser. No. 11/575,847, filed Jul. 2, 2008, now U.S. Pat. No. 8,034,979, which is a U.S. National Stage application of International Patent Application No. PCT/US2005/034186, filed Sep. 23, 2005, which claims the benefit of U.S. Ser. No. 60/637,172, filed Dec. 17, 2004, and U.S. Ser. No. 60/612,597, filed Sep. 23, 2004, the entire disclosures of which are all incorporated herein by reference.

The claimed invention was made by or on behalf of Monsanto Company and Akzo Nobel, parties to a joint research agreement in effect before the date of the claimed invention, and as a result of activities within the scope of the joint research agreement.

FIELD OF THE INVENTION

The present invention relates to an alkali-catalyzed process for preparation of alkoxylated alkyl amines or alkoxylated alkyl ether amines with peaked distribution.

BACKGROUND OF THE INVENTION

Alkoxylated alkyl amines and alkyl ether amines, particularly ethoxylated alkyl amines and ethoxylated alkyl ether amines, have many applications in industry. They can be usefully employed as adjuvants in pesticide formulations, textile processing aids, dye transfer inhibitors, acid thickeners, detergent boosters, degreasers, anti-static agents and the like.

Alkoxylated alkyl amines and alkoxylated alkyl ether amines are materials possessing the following general structures (I), respectively:

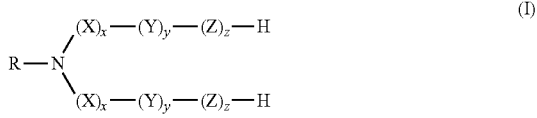

In conventional alkoxylated alkylamines, R is typically selected from a linear or branched, saturated or non-saturated alkyl group containing 8-22 carbon atoms. In alkoxylated etheramines, R corresponds to the formula:

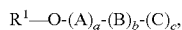

where $R^1$ is typically a linear or branched, saturated or non-saturated alkyl group containing 8-22 carbon atoms, A and B are alkylene oxide groups containing 2-4 carbon atoms, C is alkylene group containing 3-4 carbon atoms, a, b each vary from 0-5, c is 1, X, Y, Z are alkylene oxide groups containing 2-4 carbon atoms, x is 1, and y and z each independently vary from 0-15.

As illustrated by general formula (I), the alkoxylated alkyl amines/alkoxylated alkyl ether amines possess a surfactant structure which is composed of the lipophilic groups (R or $R^1$) and the hydrophilic groups (polyalkylene oxide). In their designed applications, the performance of alkoxylated alkyl amines and alkoxylated alkyl ether amines is dependent on a balance between the lipholicity and the hydrophilicity provided by these groups.

Even when the lipophilicity-hydrophilicity balance does exist, the performance of the alkoxylated alkyl amines/alkoxylated alkyl ether amines is not necessarily optimal. Traditionally, these materials are prepared from the base-catalyzed alkoxylation of the corresponding alkyl amines/alkyl ether amines. Such an alkoxylation reaction is actually the polymerization reaction of alkylene oxide that includes the characteristic propagation and chain transfer steps of the polymerization process. For this reason, the resulting alkoxylated alkylamine/alkyl ether amine is not a pure compound, but a mixture of many homologs.

As an example, FIG. 1 illustrates the homolog distribution of ethoxylated tallow amine prepared from the regular hydroxide-catalyzed ethoxylation of tallow amine with 5 moles of ethylene oxide. As shown in FIG. 1, the resulting ethoxylated product is not a single compound containing 5 ($CH_2CH_2O$) units as the general structure (structure I, with $2x+2y+2z=5$) may suggest. Instead, the product is a mixture of several homologs whose total ethylene oxide units varies from 2 to 10. Among these homologs, only those in the middle of the distribution range have the proper liphophilic-hydrophilic balance for certain applications and, therefore, are generally preferred. For example, in the case of an ethoxylated product comprising an average ratio of 5 alkylene oxide units per molecule, homologs having a desired lipophilic-hydrophilic balance typically range from 3EO to 5EO where "EO" is an ethylene oxide unit. Homologs with shorter EO chain length (<3EO) or longer EO chain length (>5EO) are not desirable for the applications for which a 5 EO/amine ratio surfactant is ordinarily prescribed, since such longer and shorter homologs are either too lipophilic or too hydrophilic for the applications utilizing this product. For at least some applications, the presence of especially long species is particularly disadvantageous, e.g., species having an EO/amine ratio of more than about 1.5× the target ratio. Therefore, it is advantageous to develop an alkoxylation process that results in alkoxylated products with peaked distribution.

Accordingly, it is an object of the present invention to develop a process for preparation of alkoxylated ethoxylated alkyl amines and alkyl ether amines, particularly ethoxylated alkylamine and ethoxylated alkyl ether amine with peaked distribution having greatly minimized drawbacks compared to those associated with the acid-catalyzed process.

U.S. Pat. No. 4,483,941 describes the preparation of ethoxylated organic materials comprising a peaked distribution of homologs, as prepared by ethoxylation in the presence of $BF_3$ and metal alkyls or metal alkoxides, $SiF_4$ and metal alkyls or metal alkoxides, or mixtures of all these catalysts. The reference lists alcohols, alkyl phenols, polyols, aldehydes, ketones, amines, amides, organic acids and mercaptans as substrates that may be ethoxylated. The patent includes a long list of amines that are subject to ethoxylation, particularly including octylamine and hexadecylamine. Working examples describe ethoxylation of $C_{12}$ to $C_{14}$ alcohols.

East German patent DD 219,478 describes the ethoxylation of amines in the presence of Lewis acid catalysts. A number of working examples are included which embody reactions with $C_{12}$ primary amine at ethylene oxide to amine ratios in the ranges of about 2, 3 and 6. At ratios of about 3 and about 6, final reaction temperatures range from 179° to 207° C.

U.S. Pat. No. 6,376,721 describes the alkoxylation of alcohols, amines, mercaptans and amides in the presence of a rare earth triflimide catalyst to obtain a peaked distribution of homologs. Working examples describe the ethoxylation of dodecanol.

Hreczuch & Szymanowski, *Recent Res. In Oil Chem.*, 2 (1998), pp. 63-76 describes ethoxylation in the presence of a calcium-based W7™ catalyst to obtain narrow range distributed ethoxylated alcohols. FIG. 6 of this reference also reflects the ethoxylation of tallowamine in the presence of this catalyst and provides a curve illustrating distribution of homologs. The reference explains that in conventional ethoxylation of an alcohol, the reaction rate constants increase for successive stages of oxyethylene, which results in a wide distribution of homologs and typically a significant fraction of unreacted alcohol. It is further explained that the kinetics of alkylamine ethoxylation are different from the kinetics of alcohol ethoxylation.

WO 02/38269 describes a catalyst comprising Ca sulfate, Ca acetate, low molecular weight Ca alcoholate and a crystalline phase in the form of organic Ca and sulfur compounds as a catalyst in the ethoxylation of alcohols to obtain a narrow distribution of homologs, and the use of such catalyst in the ethoxylation of organic substrates.

For a number of important commercial and industrial applications, it is desirable to provide alkoxylated alkyl (ether)amines that impart improved functional properties to formulations in which they are incorporated.

Among the particular applications in which alkoxylated alkylamine and alkoxylated etheramine surfactants have been used is herbicidal formulations, such as aqueous liquid glyphosate formulations comprising a salt of glyphosate, wherein they may serve to increase the efficacy of the herbicide in controlling or destroying unwanted vegetation.

N-phosphonomethylglycine, otherwise known as glyphosate, is well known in the art as an effective post-emergent foliar applied herbicide. Glyphosate is an organic compound that at neutral PH, contains three acidic protonatable groups, and in its acid form is relatively insoluble in water. Glyphosate is, therefore, normally formulated and applied as a water-soluble salt. Although monobasic, dibasic and tribasic salts of glyphosate can be made, it has generally been preferred to formulate and apply glyphosate, in the form of a monobasic salt, for example as a mono-(organic ammonium) salt such as the mono (isopropylamine), often abbreviated to IPA, salt, or as either monobasic or dibasic ammonium salt.

When the terms "ammonium", "monoammonium" and "diammonium" are used herein to refer to salts of glyphosate, these terms apply strictly to inorganic ammonium, i.e., $NH_4^+$, unless the context demands otherwise. Glyphosate rates and concentrations given herein, even where the glyphosate is present as a salt or salts, are expressed as acid equivalent (a.e.) unless the context demands otherwise.

For many applications, glyphosate salts generally require the presence of a suitable surfactant for best herbicidal performance. The surfactant may be provided in the concentrate formulation, or it may be added by the end user to the diluted spray solution. The choice of surfactant can be very important since there are wide variations among surfactants in their ability to enhance the herbicidal efficacy of glyphosate for particular applications.

Use of a highly concentrated aqueous formulation of glyphosate in the form of a salt made with the inorganic base ammonia and potassium is advantageous. Ammonia and potassium are low in cost, readily available, low in molecular weight, relatively soluble in water. Additionally, they are natural nutrients for the growth of plants and other organisms. Both potassium salts and ammonium salts have been used in substantial commercial volumes. Not all surfactants are as compatible with the potassium and ammonium salts at higher concentrations as they typically are with the isopropylamine salt, especially in concentrated aqueous liquid formulations.

The use of ammonium salts of glyphosate for preparing aqueous concentrate formulations of glyphosate suitable for killing and controlling weeds and other plants has, however, been somewhat limited due to difficulties arising from chemical and physical properties thereof, lack of suitable surfactants for preparing high-loaded liquid concentrates of such salts, reduced weed control, and requirement for complex processes for preparing liquid ammonium glyphosate compositions.

Potassium salts have recently been introduced to the market and have been highly successful. However, potassium salts are not as easy to formulate as isopropylamine salts, for example. With respect to stability, especially as reflected in the cloud points of high load concentrates, the constraints on selection and concentration of surfactants in high load potassium salt solutions are generally more limiting than in the case of isopropylamine salts.

The economical preparation of high efficacy glyphosate salt solutions depends on selecting a suitable surfactant or combination of surfactants, and providing an optimal concentration of the surfactant(s), often the highest concentration(s) that can be achieved without sacrifice of stability. Ethoxylated alkylamines have proven excellent bioefficacy in enhancing the herbicidal potency of glyphosate. However, in a concentrated glyphosate formulation with sufficient loading of the useful ethoxylated alkylamines, especially in potassium and ammonium glyphosate formulations, the formulation may not be stable at elevated temperature. Above a threshold glyphosate concentration, any substantial increase in the concentration of surfactant is typically only achievable at the expense of reducing glyphosate a.e. loading (concentration of glyphosate active). Likewise, any substantial increase in glyphosate a.e. loading of these products is often achievable only at the expense of surfactant concentration and may therefore impose a constraint on formulating to a surfactant concentration that is optimal for a desired application. Generally, it is desirable to develop an stable aqueous ammonium, potassium, or mixed salts glyphosate formulation (i) having high glyphosate a.e. loading, (ii) containing an ethoxylated alkylamine surfactant, and (iii) having a high enough concentration of that surfactant to provide formulation stability and efficacy sufficient for the application for which a given formulation is prepared. There is a constant objective of providing formulations of improved herbicidal efficacy, improved storage and handling characteristics, or reduced cost, or which meet two or more of such criteria.

In this context, a $C_8$ to $C_{22}$ alkylamine substituted by reaction with two moles of alkylene oxide, i.e., a bis(hydroxyalkyl)amine has a high degree of compatibility with a glyphosate salt, but limited value as an adjuvant to enhance the efficacy of the herbicide. $C_8$ to $C_{22}$ alkylamines having longer chain alkylene oxide substituents are more effective as adjuvants but are not as compatible with concentrated aqueous solutions of glyphosate salts, and may cause the formulation to suffer from a relatively low cloud point, e.g., <35° C. For certain herbicidal applications, the optimal surfactant may typically have an average alkylene oxide to amine ratio between about 3 and about 6. But even where the surfactant possesses such an average ratio, it may contain some unavoidable fractions of <3:1 (EO to amine ratio) and >6:1 species, the presence of which can detract from either performance properties or stability of the formulation. In this case, species having a ratio of >8:1 may have a particularly adverse effect on stability. However, there are other applications where glyphosate formulations may typically include a surfactant wherein the average alkylene oxide to amine ratio is in the range of about 8 to about 12, or about 12 to about 18. Aqueous liquid concentrates comprising the latter surfactants are formulated in a manner which preserves stability despite the relatively long alkylene oxide chains, but it remains preferable to minimize the concentration of homolog species that are well above the target, e.g., in the case of a surfactant designed to have a ratio between 8 and 12, it may be preferable to minimize the fraction of homologs having an alkylene oxide/amine ratio >12:1, or in the case of a surfactant designed to have a ratio between 12 and 18, it may be preferable to minimize the fraction wherein the ratio is greater than about 20:1 or 22:1.

SUMMARY OF THE INVENTION

The present invention generally relates to an alkoxylation process for the preparation of alkoxylated alkyl amines/alkoxylated alkyl ether amines with peaked distribution, to the products prepared therefrom and applications of same. Specific processes are described for the preparation of ethoxylated alkylamines including a Lewis acid catalyzed process and a process of the present invention while promoting the peaked distribution of the ethoxylated products.

The present invention particularly relates to ethoxylated alkylamines and alkyletheramines that exhibit favorable compatibility with glyphosate and to glyphosate formulations comprising same. The specific ethoxylated alkylamines and alkyletheramines of the invention possess a relatively high concentration of the mid-range homologs that enables them to be compatible with glyphosate herbicide actives while retaining their characteristic adjuvancy. The ethoxylated alkylamines of the invention may further be useful in the preparation of glyphosate formulations of enhanced compatibility as compared to similar formulations which incorporate alkoxylated alkylamines of the prior art having a relatively flat or wide distribution of homologs.

DETAILED DESCRIPTION OF THE INVENTION

Figure 1:
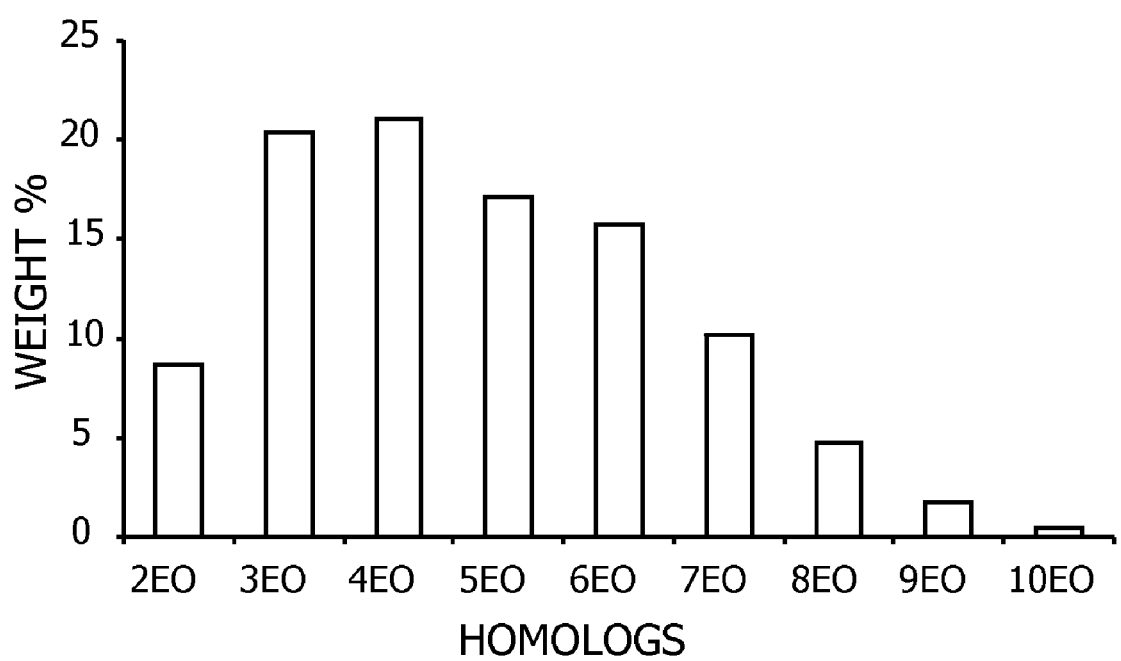
FIG. 1: Homolog distribution of tallow amine prepared with 5 moles of ethylene oxide by the regular hydroxide-catalyzed process.

Alkoxylated alkyl amines and ethoxylated alkyl ether amines of the invention are materials possessing the following general structure (I):

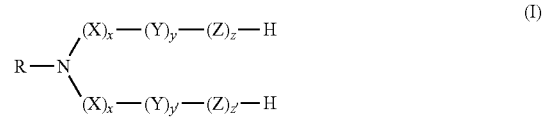

wherein R is selected from a linear or branched, saturated or non-saturated alkyl group containing 8-22 carbon atoms or a group of the formula

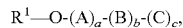

where $R^1$ is selected from a linear or branched, saturated or non-saturated alkyl group containing 8-22 carbon atoms, A and B are alkylene oxide groups containing 2-4 carbon atoms, C is alkylene group containing 2-4 carbon atoms, a, b each vary from 0-5, c is 1, X, Y, Z are alkylene oxide groups containing 2-4 carbon atoms, x is 1, and y, y', z and z' each independently vary from 0-15.

By utilizing the terminology "alkoxylated alkyl(ether)amine", it is to be understood herein that the present inventors intend either or both of alkoxylated alkyl amines and alkoxylated alkyl ether amines. The alkoxylated alkyl amine/alkyl ether amine compositions of the invention are not single compounds as suggested by their general structure (I), but rather, they comprise a mixture of several homologs having varied polyalkylene oxide chain length. Among the homologs, only those with the number of total alkylene oxide units per mole of amine closer to the most prevalent alkylene oxide adduct are preferred; homologs whose number of total alkylene oxide units is much lower or much higher than the most prevalent alkylene oxide adduct are undesirable since they are too liphophilic or too hydrophilic to be suitable for the application for which the alkoxylated alkylamine/alkyl ether amine are designed. In certain applications, for example, as surfactants in certain herbicidal formulations, the homologs having alkylene oxide chains significantly longer than average are particularly disadvantageous with respect to stability.

Alkoxylated alkyl amines and alkoxylated alkyl ether amine are prepared from the reaction of the corresponding primary alkyl amine/alkyl ether amine with a selected number of moles of alkylene oxide. Using ethoxylated alkylamines (V) as an example, the prior art generally describes the synthesis of ethoxylated alkyl amines in a two-stage process:

1) Reaction of two moles of ethylene oxide with the primary alkylamine (II) to yield the intermediate (III) (N,N-bis-(2-hydroxyethyl)N-alkylamine). No catalyst is required for this reaction.

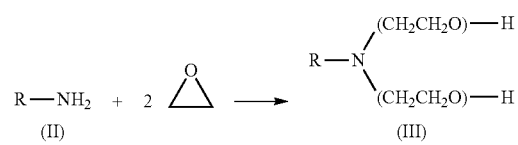

2) Reaction of additional moles of ethylene oxide with the intermediate (III) to yield the desired final ethoxylated alkylamine product (V) not having a peaked distribution. This reaction requires the use of a catalyst.

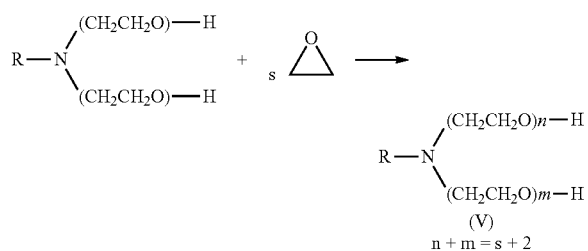

$$n + m = s + 2$$

Based on the type of catalysts, there are two types of ethoxylation processes described in the prior art. In the regular ethoxylation process commonly used in industry, the catalyst is a base, preferably a hydroxide such as sodium hydroxide or potassium hydroxide. We denote this as the "R" process. With this catalyst, the rate of the ethoxylation reaction is fast, and the formation of by-products, e.g., oxygenated hydrocarbons such as dioxane, and various (poly)ethylene glycol derivatives (EGDs), is minimal. However, the catalyzed ethoxylation in the second stage follows a polymerization mechanism that includes its characteristic propagation and chain transfer steps. As a result, the ethoxylated product obtained does not have a peaked distribution of total ethylene oxide substitution and possesses higher concentration of the undesired (too lipophilic/too hydrophilic) homologs.

As recounted above, the prior art also describes another ethoxylation process designed to obtain a preferred peaked distribution of alkoxylated alcohols, aldehydes, ketones, or alkylamines. We denote this as the "S" process. In this process, the ethoxylation is catalyzed by a Lewis acid, preferably Boron Trifluouide, and follows a different mechanism. The resulting ethoxylated product possesses a peaked distribution, with highest concentration is of the homologs generally in the middle of the distribution range, or in any event more concentrated in a desired region than the homologs of an alkoxylated alkylamine. Because the concentration of the undesired homologs is lower in this case, the performance of the ethoxylated alkylamine/alkyl ether amine in the applications they are designed for is optimized. Still other processes for producing peaked distribution alkoxylated organic compounds use calcium or rare earth based catalysts.

However, so far as is known, neither peaked distribution alkoxylated alkylamines nor peaked distribution alkoxylated etheramines have been commercially available, and the use of alkoxylated alkylamines or etheramines has not been described in applications such as herbicidal formulations, or, more particularly, herbicidal formulations comprising glyphosate salts. One of the objects of the present invention is to cover the glyphosate formulations with any alkylamines and etheramines with peaked EO distribution.

Generally, the peaked distribution alkoxylated alkylamines and etheramines of the present invention can be prepared by any process which provides the favorable distribution and/or favorable properties described herein.

Preferably, alkoxylation is conducted according to one or the other of two novel processes.

One process, the "S" process, utilizes a Lewis acid catalyst of the type taught by the prior art, but under conditions which differ from those employed in known prior art processes for alkoxylation of alkylamines. The other and generally preferred process, which we denote as the "N" process, optionally uses an alkaline catalyst of the type used in the conventional ("regular") process for the commercial manufacture of alkoxylated alkylamines, but proceeds under a set of conditions which nonetheless affords a peaked distribution by comparison to the commercially available surfactants.

According to the "S" process, an alkylamine or etheramine is reacted with an alkylene oxide in the presence of a Lewis acid catalyst, preferably boron trifluoride, within a preferred temperature range. It has been discovered that the ethoxylated alkylamines and alkyletheramines prepared from such a process exhibit improved compatibility with glyphosate while retaining their characteristic adjuvancy. Alternative catalyst systems promoting the peaked distribution can also be employed, and it is believe that the products prepared from the ethoxylation utilizing these alternative catalyst systems may also be useful in the context of the present invention. An example of such a system can be found in, for example, U.S. Pat. No. 6,376,721 which utilizes a rare earth triflimide catalyst.

The typical "S" ethoxylation process according to the invention also involves two stages. In Stage 1, the formation of the intermediate (V) (N,N-bis(2-hydroxyethyl)-N-alkylamine or etheramine), is the same as that for the regular "R" process. In this stage, the intermediate (V) is prepared via the reaction of one mole of the selected alkyl (or alkylether) amine with two moles of the ethylene oxide or other alkylene oxide at temperature that varies preferably in the range from 160-190° C. and at pressure that preferably varies from 40-90 psig. Typically, the intermediate (V) is prepared immediately prior to its catalyzed ethoxylation. However, for products based on tallow or coco amine, the Stage 1 can be by-passed by using the commercially available N,N-bis(2-hydroxyethyl)-N-alkylamine based on coco amine (Ethomeen C/12 from Akzo Nobel, Varonic K-202 from Degussa) or based on tallow amine (Ethomeen T/12 or Varonic T-202).

In the second stage of the "S" process, the intermediate (V) is reacted with additional quantity of ethylene oxide or other alkylene oxide in the presence of a catalyst. This catalyzed ethoxylation stage involves the mixing of the intermediate (V) with the desired catalyst in a pressure vessel, followed by the slow addition of the desired quantity of the ethylene oxide to the vessel while the temperature of the mixture in the vessel is carefully maintained in a certain range. The catalyzed ethoxylation of the intermediate (V) is an exothermic reaction and cooling is required to maintain the temperature in the preferred range.

However, unlike the "R" processes that utilize a basic (hydroxide) catalyst, Stage 2 of the "S" process utilizes a Lewis Acid catalyst. Boron trifluoride is the preferred catalyst, although other Lewis acid catalysts could be employed. Alternatively, said Lewis Acid catalyst can be tin fluoride ($SnF_4$), or a boron trifluoride complex. Examples of a boron trifluoride complexes useful in the context of the present invention include, but are not limited to members selected from the group consisting of boron trifluoride-ethylene oxide, boron trifluoride-diethyl ether, boron trifluoride-dibutyl ether, boron trifluoride-tetrahydrofuran, boron trifluoride-methanol, boron trifluoride-phosphoric acid and boron trifluoride-acetic acid and mixtures thereof.

In a preferred embodiment, boron trifluoride ($BF_3$) is the catalyst for the ethoxylation of alkylamine, and it is most effective when used at the $BF_3$ concentration ranging from 0.04-0.07% of the weight of the final ethoxylated product.

In addition to the catalyst, temperature is a critical factor in the new "S" ethoxylation process. In the "R" processes with the base (hydroxide) catalyst, the temperature can be anywhere between 110-190° C. However, for the "S" process of the present invention, it is preferred that the temperature be maintained in the range between 95-130° C., preferably in the range of 110-120° C. The normal catalyzed ethoxylation reaction of the intermediate (IV) does not occur at temperature higher than about 130° C. (possibly due to the destruction of the catalyst-ethylene oxide complex) or lower than about 95° C.

One of ordinary skill in the art recognizes that there are various processes for making the peaked ethoxylates employed in the present invention and any of such ethoxylates, regardless of the method of their preparation, meeting the definition of degree of peaking herein are equally useful in the context of the invention.

Whereas the acid-catalyzed process (the "S" process) promotes the peaked ethoxylation distribution and thus enhances the performance of the resulting ethoxylated alkylamine/alkyl ether amine, there are several drawbacks, including but not limited to the following that restricts its utilization and usefulness.

The catalyst (Boron Trifluoride) is not only expensive, but also a hazardous material. The use of this catalyst requires elaborated equipment for its storage and charging to the reactor.

The process also enhances the formation of undesired by-products, most noticeably dioxane and (poly)ethylene glycol derivatives (EGDs). Depending on the number of moles of ethylene oxide used in the ethoxylation process, the dioxane content in the ethoxylated products could be as high as 25000 ppm. Dioxane is perceived as a hazardous material and it is desirable that it be removed or minimized in the ethoxylated product. Because of its reasonable volatility, dioxane can be removed, e.g., by sparging the ethoxylation reaction product with nitrogen. However, removal of such a high concentration of dioxane requires additional equipment, greatly prolongs the cycle time and reduces the product yield. The concentration of EGDs may typically range from about 5% to about 10% by weight, much higher than that of dioxane. While it is not a hazardous material, the high content of EGDs lowers the concentration of the desired ethoxylated alkylamine, and thus may adversely affect the performance or effectiveness of the ethoxylated product in its application. Moreover, the EGDs are of substantially lower volatility than dioxane, and thus more difficult to separate from the alkoxylated amine surfactant.

The color of the resulting ethoxylated product degrades over time.

The process cannot be effectively utilized with propylene oxide.

The preferred process of the present invention, the "N" process, possesses the advantages of the above-described base-catalyzed and acid-catalyzed processes while eliminating or greatly reducing the drawbacks inherent in same. Specially, the "N" process enables the preparation of alkoxylated alkylamine/alkyl ether amine with the desired peaked alkoxylation distribution, thus ensuring optimum performance in their respective applications. Simultaneously, the "N" process utilizes a base catalyst, preferably a hydroxide or may in some embodiments proceed without a catalyst. As a result, the problem associated with the use of the acid-catalyst, including high cost and hazardous property of the catalyst, the formation of hazardous, undesired by-products, the prolonged cycle time, and the color degradation, are greatly minimized.

In accordance with the invention, the present inventors have discovered that polymerization can be conducted without the necessity of utilizing a catalyst, such as a Lewis acid, calcium-based or rare earth catalyst while achieving a more favorable peaked distribution of homologs than is found in otherwise identical commercially available surfactants having the same average total of alkylene oxide substituents. The preferred process, the "N" process, may optionally use an alkaline catalyst while still preserving the favorable peaked distribution that distinguishes the surfactant of the invention from the products of commerce. The novel process achieves the desired result by control of the conditions of the reaction and especially the temperature thereof. For alkoxylated alkylamines of modest average number of alkylene oxide units, it has surprisingly been discovered that the reaction can be conducted entirely in the absence of any catalyst. Because the reactivity of the growing alkylene oxide chain declines with chain length, it is preferred that an alkaline catalyst be used during a portion of the conversion where the target average alkylene oxide to amine ratio is greater than about 6. Depending on the selection of amine, selection of alkylene oxide, exact process conditions and nature of the process equipment available, it may be preferable to conclude the alkoxylation in the presence of an alkaline catalyst at average alkylene oxide/amine ratios of about greater than about 6 or 7.

Using the ethoxylation of primary alkyl amine as an example, the process of the invention, the "N" process, can be illustrated by the following three stages:

1. Stage 1 of the "N" process: Uncatalyzed ethoxylation of the primary alkylamine In this stage, the starting primary alkylamine (II) is reacted with u moles of alkylene oxide, typically about 2 moles of ethylene oxide at high temperature to yield the same tertiary intermediate (III) (N,N-bis-(2-hydroxyethyl)N-alkylamine)

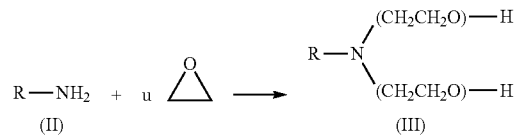

The reaction temperature varies from 160-190° C. and pressure varies from 40-90 psig. Typically, the intermediate (III) is prepared immediately prior to its further alkoxylation. However, for ethoxylated products based on tallow or coco amine, the Stage 1 can be by-passed by using the commercially available N,N-bis(2-hydroxyethyl)-N-alkylamine based on coco amine (Ethomeen C/12 from Akzo Nobel, Varonic K-202 from Degussa) or based on tallow amine (Ethomeen T/12 or Varonic T-202).

2. Stage 2 of the "N" process: Further ethoxylation of the resulting tertiary amines under controlled temperature conditions.

No catalyst is necessary in this stage, and is preferably not used. Instead, the further reaction of the tertiary amine intermediate (III) with a selected additional moles (v) of ethylene oxide is promoted by the manipulation of the ethoxylation temperature. This stage yields the second tertiary amine intermediate (IV) with longer ($CH_2CH_2O$) chain length than that of the first intermediate (III)

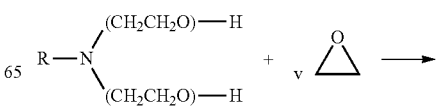

-continued

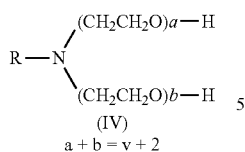
(IV)
a + b = v + 2 where a+b is greater than 2, typically greater than about 3, more typically greater than about 4, but also typically less than about 9 and more typically not greater than about 6. Where the sum of a and b meets the total target average alkylene oxide content for the ultimate surfactant product, the reaction product characterized as "intermediate (IV)" may constitute the final reaction product of the process. Where the ultimate target average number of alkylene oxide units exceeds about 6 or 7, the process preferably proceeds to stage 3.

As discovered in this invention, the peaked distribution obtained in the "N" process is possible in the stage 2 by reacting the tertiary intermediate (III) with alkylene oxide at certain temperature in the absence of a catalyst. Within the selected temperature range, the alkoxylation can proceed, and the absence of the catalyst facilitates the chain transfer between a newly alkoxylated molecule and another molecule of the tertiary intermediate (III), and results in the peaked distribution.

Both the number of moles of alkylene oxide and the alkoxylation temperature are critical factors. For the preparation of the ethoxylated products, the number of the moles of ethylene oxide used in this stage is preferred to be in the range of 1-8, typically between about 2-7, for example, in the range of 2-5. It is possible to use many sub-stages within stages 1 and 2 and end up with the same total EO addition. It is also possible to combine stages 1 and 2. However one must be mindful that ethoxylation performed in this stage with less than 2 moles of ethylene oxide normally results in final product without peaked ethoxylation distribution, while on the other hand, ethoxylation performed in this stage with more than 7 moles of ethylene oxide results in significant formation of by-products. In conducting the uncatalyzed ethoxylation, the temperature is preferably maintained in the range of about 90 to about 130° C., more preferably in the range of about 100 to about 120° C. Ethoxylation performed at lower than 90° C. or higher than 130° C. normally stops before all the ethylene oxide is consumed.

3. Stage 3 of the "N" process: Catalyzed ethoxylation
   This stage is optional. In this stage, the second intermediate (IV) is reacted with the remaining quantity of alkylene oxide to yield the final product (V). Unlike the first two stages, a catalyst is required to facilitate the ethoxylation in this stage.

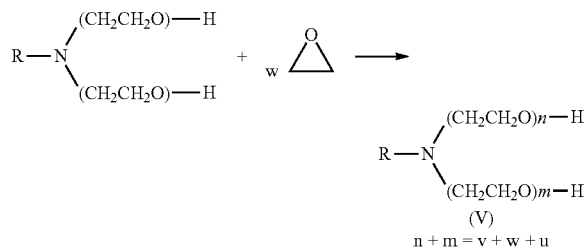
(V)
n + m = v + w + u wherein u, v and w represent the moles of alkylene oxide employed. In this optional stage, the alkoxylation is performed using the remaining quantity of alkylene oxide in the presence of a catalyst. Typically, the catalyzed alkoxylation in this stage can be performed at temperature in the range of 100-190° C., and pressure between 40-90 psig. The number of moles of alkylene oxide used in this stage varies, depending on the total number of moles of alkylene oxide used in the preparation (i.e., in all three stages). In general, to obtain maximum peaked distribution of the ethoxylated products, the number of moles of EO used in the third stage is maintained at the same or less than the number of moles of EO used in the second stage. Sodium hydroxide and potassium hydroxide are the preferred catalysts, though other hydroxide catalysts, including but not limited to lithium hydroxide, tetramethylammonium hydroxide, barium hydroxide, aluminum hydroxide, magnesium hydroxide, or complexes containing barium, magnesium and/or aluminum hydroxides, could be used. The sodium hydroxide or potassium hydroxide is most effective when the concentration of their active in the product mixture is 0.05% of the batch weight or higher.

In stages 1 and 3 of the "N" process, either or both of ethylene oxide or propylene oxide is preferably employed. Ethylene oxide is the alkylene oxide of choice in stage 2 of the "N" process. In the "N" process, the number of moles (u) is preferably about 1-3, in another embodiment 1.5-2.4, and in still another embodiment about 2.0. The number of moles (v) is generally from about 0 to about 9, in another embodiment 1-7, and in still another embodiment about 2-5. It is generally preferred that u+v is greater than or equal to 4, for example, greater than or equal to about 5 or 6. In order to achieve higher levels of ethoxylation, i.e., where u+v is greater than about 6 or 7, stage 3 with w additional moles of alkylene oxide is preferably utilized. u+v+w is generally 15 or less.

In the "N" process according to this invention, the first stage and optional third stage are similar to the two stages of the regular (the "R" process), base-catalyzed ethoxylation processes. The second stage of the "N" process according to this invention is, however, the most important, because it provides the desired peaked alkoxylation distribution.

A general comparison of the "regular" or conventional process (the "R" process) for preparing tallow amine ethoxylate having at least 8 EO and the new "N-process" of the invention for preparing same is provided below.

TABLE A

|  | Regular Process | N Process |
|---|---|---|
| Stage 1 |  |  |
| Tallowamine, mole | 1 | 1 |
| EO, moles | 2 | 2 |
| Temperature, ° C. | 160-180 | 160-180 |
| Pressure, psig | 90 maximum | 90 maximum |
| Stage 2 |  |  |
| Catalyst | NaOH/KOH | None |
| Catalyst concentration, % | ~0.2 | — |
| EO, moles | 7.0 | 4 |
| Pressure, psig | 90 maximum | 90 maximum |
| Temperature, ° C. | 160-180 | 90-130 |
| Stage 3 |  |  |
| Catalyst | — | NaOH/KOH |
| Catalyst concentration, % | — |  |
| EO, moles | — | 3 |
| Temperature, ° C. | — | 160-180 |
| Pressure, psig | — | 90 maximum |

Since water can undergo the catalyzed reaction with ethylene oxide to yield undesired by-products, it is important that all ethoxylation stages in the "R", "S" and "N" processes are performed under the anhydrous condition. To attain this condition, drying of the starting material (alkylamine or alkyl ether amine) and the ethoxylation equipment is done by heating the material and equipment to a temperature of 100-150° C. under nitrogen purging or vacuum, until the content of the water in the starting material is less than 0.1 percent, and preferably less than 0.05 percent, of its weight.

The preferred starting alkylamines include, but are not limited to, those derived from tallow, coconut oil, soybean oil, palm kernel oil, and mixtures thereof. The preferred starting ether amines include, but are not limited to, decyl ether amine, undecyl ether amine, dodecyl ether amine, tridecyl ether amine, tetradecyl ether amine, hexadecyl ether amine, octadecyl ether amine and mixtures thereof. In a preferred embodiment, it is preferred that the starting amines be of the formula:

$$R-NH_2$$

wherein R selected from a linear or branched, saturated or non-saturated alkyl group containing an average of 8-22 carbon atoms; for example, 12-22 carbon atoms; or 16-22 carbon atoms. Here the number of carbons is expressed as an average because amines derived from natural oils comprise a mixture of alkyl groups of somewhat varying length. It is generally preferred that the weight average value of R, $R^1$ or $R^2$ be between about $C_{12}$ and about $C_{22}$. In some applications, the average value is between about $C_{14}$ and about $C_{22}$ or between about $C_{16}$ and about $C_{22}$. In one embodiment, it is particularly preferred that the alkoxylated alkyl(ether)amines used in the formulations of the invention be derived from primary amines having a molecular weight greater than about 200. Amines wherein the alkyl substituent contains between 16 and 18 carbon atoms may be especially advantageous, e.g., tallowamines which offer significant economic and commercial advantages in applications such as herbicidal formulations. Alkoxylated alkylamine and alkoxylated etheramine surfactants as prepared by the preferred "N" process of the invention have not only a peaked distribution of desired homologs but also relatively low concentrations of dioxane, EGDs and other byproducts that may be detrimental to the intended end use. The dioxane content after a stripping step is typically not greater than 400 ppm, more typically not greater than 300 ppm, and still more typically not greater than 200 ppm, while the total EGDs content, including a vinyl polyethylene glycol component, is less than about 5% by weight, more typically not greater than about 4% by weight, and most typically not greater than about 3% by weight, of the resulting ethoxylated product.

To compare alkylene oxide distribution in an alkoxylated alkylamine, use of degree of peaking is helpful. The degree of peaking (Σ3) is defined as the sum of the areas for the adjacent three most prevalent peaks. The relative degrees of peaking of ethoxylates prepared according to the process of the present invention was measured and compared to their counterparts prepared via conventional base-catalyzed ethoxylation.

For degree of peaking determinations, area percent determined by gas chromatography (GC) was used. The degree of peaking is expressed as a weight percentage (%). The higher the weight percentage, the more peaked the molecular weight distribution. The formula and method for determination of molecular weight distribution can be found in Narrow Alcohol Ethoxylates, Annual Surfactants Reviews, vol. 2, Ed. D. R. Karsa (1999), and, with some modification, can be adapted for alkoxylated alkylamines.

The alkoxylated alkyl amines having peaked distribution of the present invention are further characterized in having peaked distribution defined by a degree of peaking at least 5% greater than the degree of peaking in the distribution of a conventional alkoxylated amine composition prepared via conventional base catalysis. Typically, the degree of peaking may be at least 6% greater, preferably at least 7% greater than the degree of peaking in the distribution of a conventional alkoxylated amine composition prepared via conventional base catalysis, for which the conditions are described in Table A. In still other embodiments, the degree of peaking at least 10% greater than that found in the distribution of a conventional peaked alkoxylated amine compositions prepared via conventional base catalysis.

A normalized peaking index may be defined as PI=$(W_0/2)^{1/2}(\Sigma 3)$ wherein PI is the peaking index, $\Sigma 3$ is the sum of the weight percentages of the three most prevalent homologs, and $W_0$ is the weight average ratio of alkylene oxide units per molecule in the alkoxylated alkylamine or alkoxylated etheramine composition. Preferably the PI is greater than 100, more preferably greater than about 102.

The preferred alkoxylated alkylamines with peaked distribution include, but are not limited to ethoxylated tallow amine with 3 to 15 EO, ethoxylated coco amine with 3 to 15 EO, and mixtures thereof. Preferred alkoxylated alkyl ether amines with peaked distribution include, but are not limited to ethoxylated dodecyl ether amine with 3 to 15 EO, ethoxylated tridecyl ether amine with 3 to 15 EO, ethoxylated tetradecyl ether amine with 3 to 15 EO, ethoxylated hexadecyl etheramine with 3 to 15 EO, ethoxylated octadecyl etheramine with 3 to 15 EO and mixtures thereof. In the formulation of aqueous glyphosate salt concentrates, several discrete ranges of EO/amine ratio are commonly used, e.g.: (i) a surfactant having a relatively low ratio in the range of about 3 to about 6 EO/amine, most typically about 5; (ii) a surfactant having an intermediate EO/amine ratio in the range between about 8 and about 12 EO/amine, more typically about 9 to about 11, most typically about 10; and (iii) a surfactant having a relatively high EO/amine ratio in the range between about 12 and about 18 EO/amine, more typically between about 13 and about 17, most typically about 15.

Though not required, a solvent that is inert toward the reaction with ethylene oxide can also be used to improve the handling of the starting alkylamine or the resulting ethoxylated product, or to meet the minimum initial volume of material that is required for proper mixing action with ethylene oxide as required for each ethoxylation reactor. Aromatic solvents, such as xylene, toluene, alkylbenzenes such as ethylbenzene, hexylbenzene, dodecylbenzene, alkylnaphthalenes such as methyl and dimethylnaphthalene, isopropyl- and di-isopropylnaphthalene, or commercial aromatic solvents, such as Aromatic Solvent 100, 150 or 200 available at ExxonMobil, or organic ethers, such as dibutyl ether . . . and the like are suitable solvents for the process of this invention.

Glyphosate formulations generally require one or more adjuvants in order to boost their herbicidal efficacy. The proportion of adjuvant employed in the formulation is typically 10% or higher, in order to achieve significant boosting effect. The cost associated with the use of the adjuvants in glyphosate formulations is significant. Therefore, there is an ever increasing need to find a more effective and economical adjuvant for glyphosate.

Glyphosate is an acid with a very limited solubility in water while salts of glyphosate have very high solubility in water. Therefore, glyphosate formulations usually employ salts of glyphosate. Many types of counterions have been used commercially in glyphosate products. They include isopropylammonium (IPA$^+$), monoethanolammonium (MEA$^+$), diethanolammonium (DEA$^+$), triethanolammonium (TEA$^+$), sodium, trimethylsulfonium (TMS$^+$), potassium (K$^+$), and ammonium (NH$_4^+$). Potassium glyphosate is a preferred glyphosate salt employable in the context of the invention.

For liquid aqueous glyphosate concentrates, glyphosate loading is preferably 360 g ae/l or higher. It is known to those skilled in the art that many biologically useful surfactants cannot be reliably incorporated into glyphosate formulations at glyphosate, a.e., concentrations greater than 360 g/L without risk of phase separation at elevated temperatures. For such aqueous concentrates, therefore, an objective is to select a highly efficacious surfactant that can be used at relatively low concentration in glyphosate formulations to improve significantly the herbicidal efficacy of glyphosate. It is particularly preferred to identify and select a surfactant that can be formulated into stable glyphosate formulations including potassium and ammonium salts of glyphosate, at 470-600 g ae/l.

The present invention meets such objective in providing glyphosate formulations having favorable and/or improved stability and herbicidal efficacy comprising, as an adjuvant, at least one peaked distribution alkoxylated alkylamine surfactant. The aforementioned adjuvant can be employed at low concentration and is stable in various salts of glyphosate even at very high glyphosate concentration.

It is generally preferred that the total number of moles (2x+y+y'+z+z') of alkylene oxide used for the alkoxylation of the alkyl (or alkylether)amine varies from 3-15; typically from 3-12, in many instances from 3-9.

Preferred examples of ethoxylated alkylamines according to the invention are ethoxylated versions based on cocoamine, tallow amine, soya amine, oleyl amine, palm amine and mixtures thereof.

In various exemplary embodiments, the ethoxylated amine of the invention is selected from the group consisting essentially of ethoxylated tallowamine, ethoxylated cocoamine, ethoxylated alkyletheramine such as tridecyletheramine, each having from 3 to 15 moles of EO, and mixtures thereof.

A typical stable liquid glyphosate formulation according to the invention has a concentration of glyphosate in the range of 360-600 g ae/l, preferably 450-580 g ae/l, and the ratio of glyphosate (wt % ae) to the ethoxylated alkylamine surfactant with peaked distribution is between 2:1 to 25:1. Typically, ratio of glyphosate (wt % ae) to the ethoxylated alkylamine surfactant with peaked distribution is between 2.5:1 to 20:1, more typically between 3:1 to 15:1.

The ethoxylated alkylamine with peaked distribution of the invention is exemplified by having an enhanced cloud point of about 8 degrees in 54.8% K-glyphosate formulation with 10% peaked cocoamine-5EO surfactant when compared to the regular cocoamine-5EO having the same carbon chain length and average EO chain length prepared via conventional base catalysis.

The present invention encompasses not merely formulations of glyphosate, but also relates to other herbicidal compositions comprising at least one herbicidal active, and at least one surfactant, wherein said at least one surfactant comprises the alkoxylated alkylamine and/or alkylether amine with peaked distribution of the invention. A herbicidal composition according to the invention can optionally comprise other additives such as ammonium sulfate, potassium sulfate, potassium chloride, sodium sulfate, urea, glycols, or mixtures thereof. A contemplated composition can optionally include a synergist, quick-burn additive, humectant, co-herbicide, dye, pigment, corrosion inhibitor, thickener, dispersing agent, calcium sequestrant, defoamer, antifreeze, pour-point depressant, process aids, or mixture thereof. Combinations of glyphosate salts and co-herbicide salts are specifically contemplated by the present invention. Preferably, additives used in glyphosate compositions of the present invention possess sufficient solubility or dispersibility in a concentrated aqueous potassium glyphosate solution at a pH of from about 4 to about 7 to allow desired concentrations to be attained.

Where a co-herbicide is included in the formulation, it is preferred that the co-herbicide be water-soluble, and more preferred that it be included in the form of an ammonium or potassium salt. Examples of suitable co-herbicides are the ammonium salts of acifluorfen, asulam, benazolin, bentazon, bialaphos, bromacil, bromoxynil, chloramben, clopyralid, 2,4-D, 2,4-DB, pelargonic acid, dalapon, dicamba, dichlorprop, diclofop, endothall, fenac, fenoxaprop, flamprop, fluazifop, fluoroglycofen, fomesafen, fosamine, glufosinate, haloxyfop, imazameth, imazamethabenz, imazamox, imazapyr, imazaquin, imazethapyr, ioxynil, MCPA, MCPB, mecoprop, methylarsonic acid, naptalam, nonanoic acid, picloram, sulfamic acid, 2,3,6-TBA, TCA and triclopyr. A preferred co-herbicide is the salt of glufosinate.

Formulations of the present invention may be generally prepared by mixing the glyphosate salt solution, prepared as outlined above, together with other ingredients in a suitable mixing vessel with agitation, such as a blender.

A typical aqueous concentrate according to the invention contains glyphosate acid equivalent in the range of from 30 to 45%, and from about 1.2 to about 22.5% surfactant. For application to a field in control of weeds, a typical formulation according to the invention contain glyphosate acid equivalent in the range of from about 0.1 to 18%, typically 0.1 to 5 wt. %, more typically 0.2 to 3%, most commonly 0.5 to 2 wt. %. However, stronger mixtures, e.g., in the range from about 2 to about 15% surfactant may be desirable for some applications.

This invention also relates to a herbicidal method of using a contemplated composition in an amount effective to kill or control unwanted vegetation by diluting the composition in water and applying the diluted composition to foliage of the vegetation to be killed or controlled.

The glyphosate formulation of the invention should be applied to plant foliage at an application rate sufficient to give the desired effect. Application rates are usually expressed as amount of glyphosate a.e. per unit area of land treated, e.g. grams a.e. per hectare (g a.e./ha). What constitutes a "desired effect" varies according to the standards and practice of those who investigate, develop, market and use glyphosate products. For example, the amount of glyphosate a.e. applied per unit area to give, consistently and reliably, at least 85% control of a plant species as measured by growth reduction or mortality is often used to define a commercially effective rate.

Preferred compositions of the invention provide enhanced herbicidal efficacy by comparison with commercial standard formulations of glyphosate "Herbicidal efficacy," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific glyphosate formulation, such as a formulation of the present invention, is within the skill of the ordinary agricultural scientist. Those of skill in the art will likewise recognize that individual plant conditions, weather and growing conditions, as well as the specific formulation selected, will influence the degree of biological effectiveness achieved in practicing this invention. Useful application rates can therefore depend upon all of the above conditions. Much information is known about appropriate application rates for glyphosate formulations in general. Over two decades of glyphosate use and published studies relating to such use have provided abundant information from which a weed control practitioner can select glyphosate application rates that are herbicidally effective on particular species at particular growth stages in particular environmental conditions.

Various application methods may be employed including broadcast spraying, directed spraying or wiping the foliage with a diluted composition of this invention. Depending on the degree of control desired, the age and species of the plants, weather conditions and other factors, typically the glyphosate application rate is a herbicidally effective amount of about 0.1 to about 10 kg a.e./ha and preferably from about 0.25 to about 2.5 kg a.e./ha, although greater or lesser amounts may be applied.

The alkoxylated alkylamine with peaked distribution of the invention is preferably selected so that an aqueous concentrate containing K-glyphosate wt % a.i. of 54.8 ("wt % a.i." means weight percent active ingredient, in this case K glyphosate) and the peaked distribution alkoxylated alkylamine at a concentration of 10 wt % exhibits a cloud point greater than about 66° C. More particularly, in a potassium glyphosate concentrate of such composition, a formulation containing 10 wt % of a peaked distribution cocoamine 5EO surfactant has a cloud point approximately 8° C. higher than the otherwise identical formulation containing 10 wt % of a conventional cocoamine 5EO surfactant made by conventional base catalysis. Other otherwise identical K glyphosate solutions containing conventional alkoxylated alkylamine surfactants typically possess a cloud point of room temperature, or slightly above room temperature.

A typical stable liquid glyphosate formulation according to the invention has a concentration of glyphosate in the range of 360-600 g ae/l, preferably 450-580 g ae/l, and the ratio of glyphosate (wt % ae) to the ethoxylated alkylamine surfactant with peaked distribution is between 2:1 to 25:1. Typically, ratio of glyphosate (wt % ae) to the ethoxylated alkylamine surfactant with peaked distribution is between 2.5:1 to 20:1, more typically between 3:1 to 15:1. In exemplary embodiments of such formulations, the ratio of glyphosate (wt % ae) to the alkoxylated amine surfactant with peaked distribution may be between 3.5:1 to 8:1, or in particular instances between 4:1 to 6:1.

Although it is an important objective of the invention to provide surfactants suitable for producing stable high load aqueous liquid concentrates comprising potassium and ammonium glyphosate, it will be understood that the surfactants of the invention can also be used in solid glyphosate acid and glyphosate salt formulations. Ammonium and diammonium glyphosate, in particular are often supplied in dry, solid granular form. Dry formulations comprising sodium salts of glyphosate and or comprising glyphosate acid are also known. In this context, it will be understood that the term "stable" applies in the sense that formulations comprising the surfactants of the invention are formulated so as to avoid excessive stickiness and/or syneresis.

The present inventors have established that superior properties are exhibited by the surfactants prepared by the novel processes described herein, and in particular that surfactants of the invention are distinguished by the distinctly higher cloud points compared to the cloud points exhibited by exemplary aqueous glyphosate salt concentrates which contain these surfactants. Thus, for example, the surfactants of the invention may be characterized by reference to an aqueous concentrate containing potassium glyphosate salt in a concentration of 54.8 wt. % of the active ingredient salt ("a.i.").

Such formulation containing an alkoxylated alkylamine or alkoxylated etheramine of the invention has a cloud point at least 3° C. higher, preferable at least 5° C. higher, and in another embodiment at least 7° C. higher than that of substantially similar glyphosate formulations containing conventional non-peaked ethoxylated alkylamines having the same distribution of carbon-chain length, and the same average EO chain length, prepared by conventional base catalysis, which is hereinafter defined as catalysis according to the conditions described in Table A, as the surfactant component.

Additionally, where alkoxylation is conducted in the substantial absence of catalyst until the average extent of substitution, i.e., the weight average value of the sum of $(2x+y+y'+z+z')$ sometimes referred to herein as "$W_0$," has reached a value of 4, 5, 6, 7, 8 or 9, the surfactants of the invention contain relatively lower amounts of dioxane and EGDs including, but not limited to vinyl polyethylene glycols.

It has been established that superior properties are exhibited by the surfactants prepared by the novel processes described herein, and in particular that surfactants of the invention are distinguished by the distinctly higher cloud points that are exhibited by exemplary aqueous glyphosate salt concentrates which contain these surfactants. Thus, for example, the surfactants of the invention may be characterized by comparison of the cloud points exhibited by a pair of reference aqueous concentrates, each consisting of potassium glyphosate salt in a concentration of 540 g/L, a.e., 5.5 wt. % alkoxylated alkyl(ether)amine surfactant having EO groups, and 4.5 wt. % bis(2-hydroxyethyl)cocoamine. A first such reference formulation containing an adjuvant surfactant of the invention exhibits a cloud point at least about 3° C. higher than the cloud point of a second reference formulation of identical composition but containing 5.5 wt. % of a reference surfactant rather than the adjuvant surfactant of the invention. For purposes of this comparison, the surfactant of the invention and the reference surfactant are each derived from a primary amine having a molecular weight of at least 200 (thus have the same distribution of carbon chain length), and have the same value of $W_0$ as defined herein. The reference surfactant is prepared by an NaOH-catalyzed reaction of the amine with alkylene oxide conducted under conventional conditions described hereinbelow.

Additionally, where alkoxylation is conducted in the substantial absence of catalyst until the average extent of substitution, i.e., the number average value of the sum of $(2x+y+y'+z+z')$ sometimes referred to herein as "$W_0$," has reached a value of 4, 5, 6, 7, 8 or 9, the surfactants of the invention preserves a relatively low concentration of dioxane, vinyl PEGs, and other EGDs.

It has further been observed that the frequency distribution of homologs in the surfactants of the invention typically differs in various ways from the frequency distribution for the homologs of the conventional alkoxylated alkylamine and alkoxylated etheramine surfactants of commerce. For example, in most instances, the degree of peaking is higher in the surfactants of the invention. The degree of peaking is defined as the sum of the number percentages of the three most prevalent homologs. For the surfactants of the invention, this sum, sometimes referred to herein as "$\Sigma 3$," is in most instances higher by an increment of at least about 2 wt. %, more typically at least about 3%, often at least about 4 wt. %, 5 wt. %, or 6 wt. %, basis the entire surfactant, than the $\Sigma 3$ value for a reference mixture of homologs having the same value of $W_0$, the same frequency distribution with regard to the number of carbon atoms in the substituent R, and the same identity of X, Y and Z as the surfactant of the invention. It has further been noted that the ratio of the degree of peaking for the surfactants of the invention to the corresponding reference mixture is typically at least about 1.05, more typically at least about 1.07 or 1.08, and in a majority of cases at least about 1.10. For purposes of this comparison, the reference mixture is an alkoxylated alkylamine or etheramine characteristic of the prior product of commerce, and is prepared by NaOH-catalyzed reaction of $RNH_2$ with alkylene oxide conducted entirely under autogenous pressure up to 90 psig at a temperature of 160° to 180° C. and an NaOH concentration of 0.2 wt. %. It will be understood that, while not all commercial surfactants are necessarily prepared under the exact conditions here specified for the "reference mixture," a surfactant of the invention which has a degree of peaking at least about 3 wt. % higher (or even 2 wt. % higher) than this reference composition will in at least most instances also have a degree of peaking higher than known commercially available alkoxylated amine surfactants which have the same values of $W_0$ and $\Sigma3$ as the inventive and reference surfactants, the same frequency distribution with regard to the number of carbon atoms in the substituent R, and the same identify of X, Y and Z.

The degree of peaking varies with value of $W_0$, generally inversely therewith, For purposes of comparison, the degree of peaking may be normalized across a range of values for $W_0$ by definition of a "peaking index," computed by multiplying $\Sigma3$ by a function of $W_0$. For example a peaking index may conveniently be defined as $(W_0/2)^{1/2}(\Sigma3)$. As so defined, the peaking index for the surfactant of the invention is typically greater than the peaking index for the corresponding reference mixture by an increment of at least about 3, more typically at least about 5, 6, or 8%. The ratio of the peaking index for the surfactants of the invention to the peaking index for the corresponding reference surfactants is typically at least about 1.05, more typically at least about 1.07 or 1.08, and in most instances at least about 1.10.

However, it has further been observed that the homolog frequency distribution pattern varies somewhat among the surfactants of the invention, as it also does among the surfactants of the commerce. In a limited number of instances, analyses of the surfactants of the invention have indicated a degree of peaking and peaking index that have appeared to be actually lower than those of the comparative reference mixture, yet the novel surfactants still exhibit superior properties with respect to the cloud point of glyphosate salt concentrates. It is possible that these aberrant results have been attributable to analytical error, but also possible that they accurately reflect the samples analyzed.

Even though not all surfactants of the invention are necessarily distinguished from the corresponding reference mixture or product of commerce by the degree of peaking or the peaking index, the homolog distribution for the surfactants of the invention also typically differs from the distribution for conventional alkoxylated surfactants of the prior art with respect to certain other characteristics. Among these are what may referred to as the "tailing index" and the "tilt ratio." With regard to stability of aqueous glyphosate salt concentrates, especially potassium or ammonium salt concentrates, it is generally preferred that a surfactant of given value for $W_0$ have a relatively low concentration of homologs whose degree of substitution, i.e., the value of $(2x+y+y'+z+z')$, is significantly greater than $W_0$. Generally it is preferred that there not be a significant fraction of homologs whose number % prevalence $(W_i)$ excess $1.5(W_0)$. For this purpose a tailing index may be defined as either $\beta_1$, $\beta_2$, $\beta_3$, $\beta_{12}$, or $\beta_{23}$ where:

$\beta_1$ is the sum of the number percentages of homologs $W_i$ from i=k to infinity where $W_i$ is the number percentage of the homolog in which i equals the sum of the number of alkylene oxide substituents $(2x+y+y'+z+z')_i$;

$\beta_2$ is the sum of the number percentages of homologs $W_i$ from i=k+1 to infinity;

$\beta_3$ is the sum of the number percentages of homologs $W_i$ from k+2 to infinity;

$\beta_{12}=\beta_2+[(k+1)-W_0]/W_k$;

$\beta_{23}=\beta_3+[(k+1)-W_0]/W_{k+1}$; and k is an integer such $(W_0-1)<k\leq(W_0)<(k+1)$.

Related to the tailing index is a parameter that may be defined as the tilt ratio, a quotient of the sum of proportions of homologs having relatively low values of $(2x+y+y'+z+z')$ over the sum of proportions of homologs having relatively high values for $(2x+y+y'+z+z')$. For example, an overlapping tilt ratio may be defined as $\alpha_{23}/\beta_{12}$ or $\alpha_{23}/\beta_{23}$ where:

$\alpha_2$ is the sum of the number percentages of homologs $W_i$ from i=2 to k $\alpha_{23}=\alpha_2+(W_0-k)W_{k+1}$ and $\beta_1$, $\beta_2$, $\beta_{12}$, and $\beta_{23}$ are defined above, in which case $\alpha_{23}/\beta_{23}$ may preferably be greater than about 1.42. It has also been observed that the tilt ratio varies with the value of $W_0$, so that: where $W_0$ is between 3 and 4.5, the tilt ratio $\alpha_{23}/\beta_{23}$ is at least about 1.90; where $W_0$ is between 4.5 and 5.5, the tilt ratio $\alpha_{23}/\beta_{23}$ is at least about 1.85; where $W_0$ is between 5.5 and 6.5, the tilt ratio $\alpha_{23}/\beta_{23}$ is at least about 1.75; where $W_0$ is between 6.5 and 8.5, the tilt ratio $\alpha_{23}/\beta_{23}$ is at least about 1.40; where $W_0$ is above 8.5, the tilt ratio $\alpha_{23}/\beta_{23}$ is at least about 1.42. Other empirical functions may provide alternative definitions of tailing index, tilt ratio and peaking index.

Generally, the tilt ratio $\alpha_{23}/\beta_{23}$ differs from the same ratio for the corresponding reference mixture by an increment of at least about +0.08, more typically at least about +0.10, and in most instances at least about 0.15. The ratio of the tilt ratio for the surfactant of the invention to the tilt ratio for the reference mixture is ordinarily at least about 1.05, more typically at least about 1.0, and in a majority of cases 1.15.

Because the peaking indices, tailing indices and tilt ratios reflect empirical observations of the surfactants of the invention vs. the comparative reference mixtures that are indicative of the alkoxylated alkylamines and etheramines of commerce, it will be understood that there are variations from specimen to specimen whereby the range of values for the novel surfactants and the range of values for the reference mixtures and commercial surfactants can at least potentially be found to overlap with regard to at least one of these indices and perhaps in some instances with all of them. At the time of this application, that matter has not been fully explored. Thus, it is important to understand that the fundamental differences between the surfactants of the invention and those of the prior art is found in their respective effect on the cloud points of aqueous glyphosate salt concentrates, especially those comprising potassium and ammonium salts; and, of course, in the processes by which they are respectively prepared. In preferred embodiments, the surfactants of the invention also differ from prior art surfactants prepared by Lewis acid catalysis with respect to the concentration of dioxane, vinyl PEG and other EGDs.

Nevertheless, it is believed that, in general, the surfactants of the invention differ from the reference mixtures, and therefore from the prior art commercial surfactants, with respect to at least one of the parameters discussed above, i.e., the degree of peaking, the peaking index, the tailing index, and/or the tilt ratio, or by some combination thereof; at that these parameters have value in helping to characterize the surfactants of the invention.

The invention will now be illustrated by the following nonlimiting examples.

Example 1

Preparation of Ethylated Coco Amine by the "S" Process Using 5 Moles of Ethylene Oxide Distilled coco amine (520 g, 2.6 moles) was charged to a one-gallon stainless steel pressure vessel and then heated at 130° C. under nitrogen purging for 30 minutes to reduce its moisture content to less than 0.1%. Ethylene Oxide (230 g, 5.23 moles) was then added to the pressure vessel over a period of 40 minutes while the temperature was maintained at 150-160° C. Following a 30-minutes period of digestion, the reaction mixture was purged with nitrogen to remove the trace of ethylene oxide and analyzed. Its Total Amine Value is 194 mg KOH/g, indicating that the 2.00 moles of ethylene oxide has been consumed for the ethoxylation of 1 mole of coco amine.

The product mixture was then cooled to 100° C. Boron Trifluoride-Phosphoric Acid complex (1.70 g) was then injected to the reactor. The mixture was then heated to 110° C., then ethylene oxide (330 g, 7.5 moles) was added to the reactor over a 90 minutes period while the pressure was maintained at 50 psig. An exothermic reaction occurred; cooling was applied to maintain the temperature in the range of 110-120° C. throughout the addition of ethylene oxide. Upon completion of the ethylene oxide addition, the reaction mixture was digested for one hour at the same temperature and pressure. Analysis showed that the product mixture contains about 2000 ppm of dioxane. A combination of nitrogen purging and the in injection of water (to generate steam in situ) was then applied for two hours to strip the dioxane from the product mixture. The product mixture was then dried by nitrogen purging at 120° C. for one hour to reduce its moisture content to less than 0.5%. Its TAV is 133.4 mg KOH/g, indicating that a total of 5.0 moles of ethylene oxide have been consumed for the ethoxylation each mole of coco amine.

Figure 2:
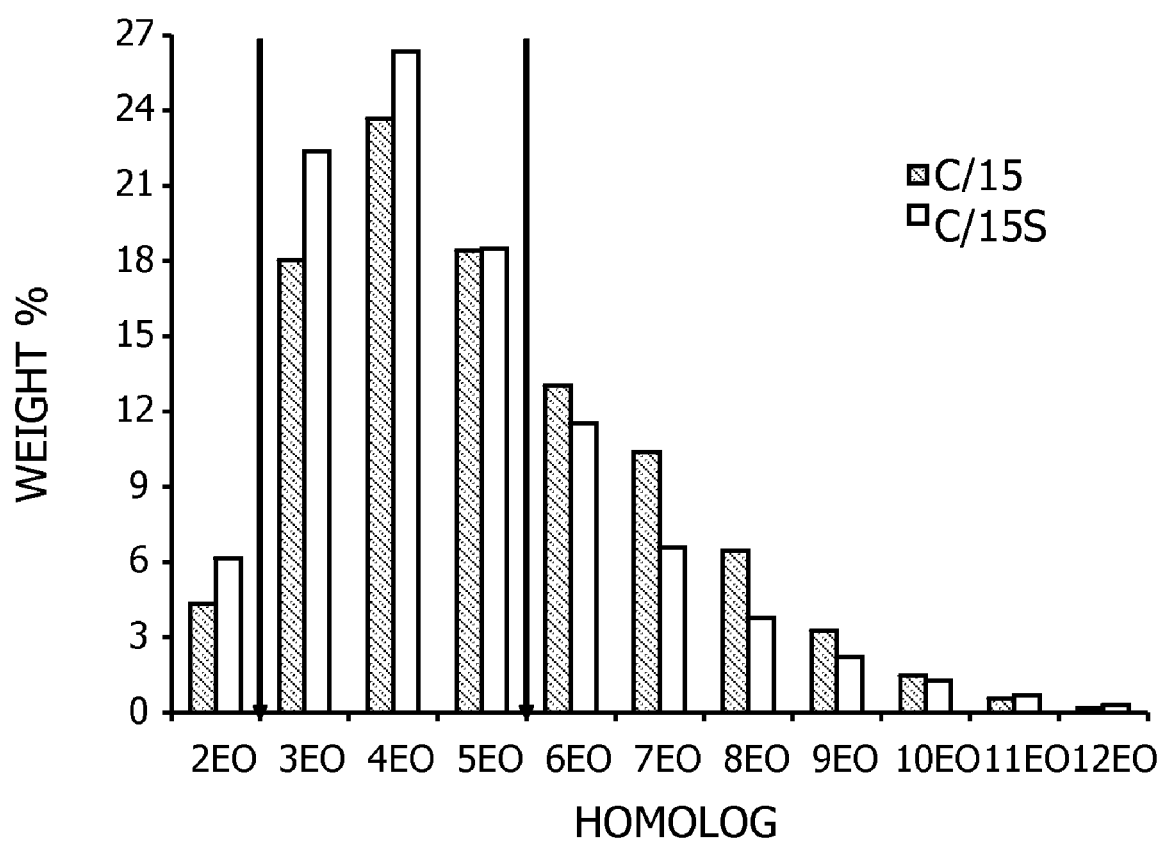
FIG. 2: Homolog distribution of ethoxylated coco amine prepared with 5 moles of ethylene oxide by the "R" process (C/15) and "S" process (C/15S).

FIG. 2 illustrates the homologs distribution of the resulting product (C/15S) and of the Ethomeen C/15, its commercially available counterpart that is prepared by the regular, hydroxide-catalyzed ethoxylation of the cocoamine with the same number of moles (5) of the ethylene oxide. The peaked distribution of the homologs is indicated by their higher concentration (weight %) at the middle of the distribution range. As is shown in FIG. 2, the most prevalent EO adduct is 4 in both processes even though 5 EO is added. The degree of peaking is 68 for C/15S and 60 for C/15.

Examples 2

Preparation of Ethoxylated Cocoamine by the "S" Process Using 6 Moles of Ethylene Oxide In this example, the first stage (ethoxylation of distilled cocoamine with 2 moles of ethylene oxide) was by-passed. The commercially available Ethomeen C/12 was used as the starting material. The ethoxylated of the Ethomeen C/12 with 4 moles of ethylene oxide in this example was catalyzed by Boron Trifluoride-Diethyl Ether Complex.

Ethomeen C/12 (750 g, 2.59 moles) was charged to a one-gallon stainless steel pressure vessel and then heated at 130° C. under nitrogen purging for 30 minutes to reduce its moisture content to less than 0.1%. It was then cooled 100° C. Boron Trifluoride-Diethyl Ether complex (1.56 g) was then injected to the reactor. The mixture was then heated to 110° C., then ethylene oxide (460 g, 10.45 moles) was added to the reactor over a 60 minutes period while the pressure was maintained at 50 psig. An exothermic reaction occurred; cooling was applied to maintain the temperature in the range of 110-120° C. throughout the addition of ethylene oxide. Upon completion of the ethylene Oxide addition, the reaction mixture was digested for one hour at the same temperature and pressure. Analysis showed that the product mixture contains about 3000 ppm of dioxane. A combination of nitrogen purging and the in injection of water (4% of batch weight, to generate steam in situ) was then applied for two hours to strip the dioxane from the product mixture. The product mixture was then dried by nitrogen purging at 120° C. for one hour to reduce its moisture content to less than 0.5%. Its TAV is 123.7 mg KOH/g, indicating that a total of 5.8 moles of ethylene oxide have been consumed for the ethoxylation each mole of the coco amine.

Figure 3:
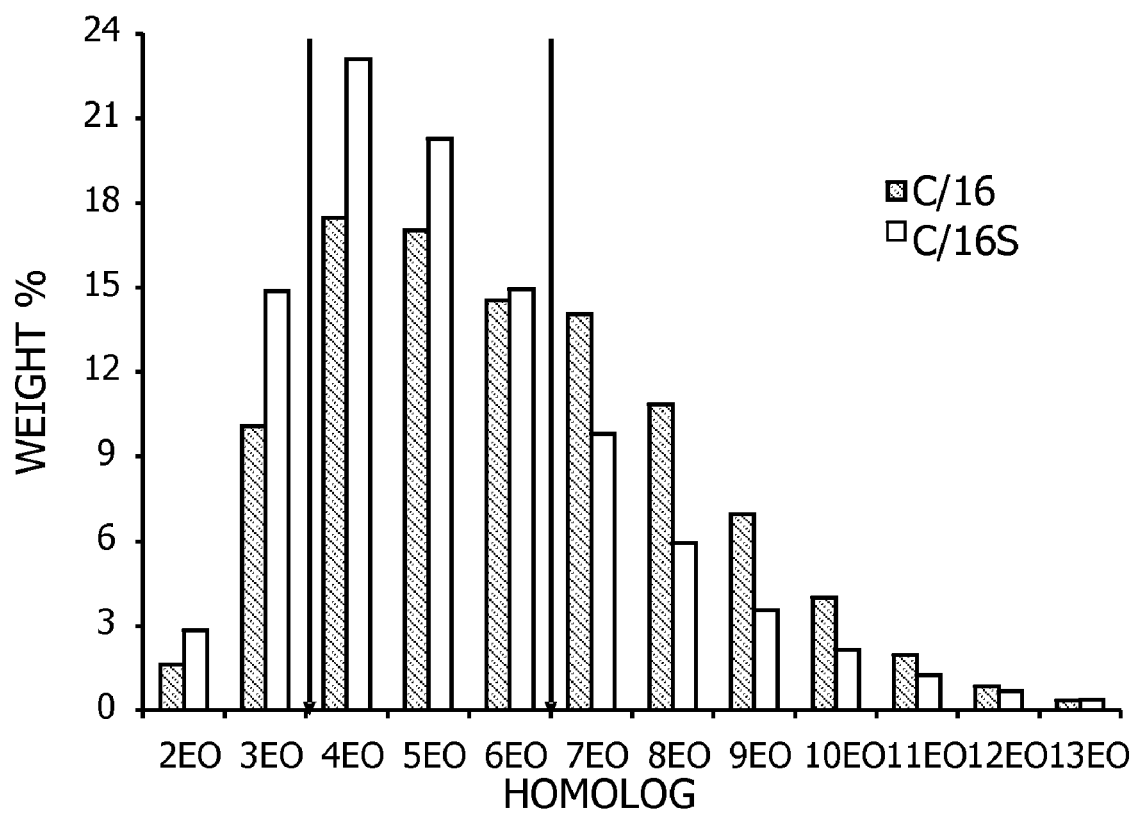
FIG. 3: Homolog distribution of ethoxylated cocoamine prepared with a total of 6 moles of ethylene oxide by the "R" process (C/16) and the "S" process (C/16S).

FIG. 3 illustrates the homologs distribution of the resulting product (C/16S) and of the Ethomeen C/16, its commercially available counterpart that is prepared by the regular, hydroxide-catalyzed ethoxylation of the cocoamine with the same number of moles (6) of the ethylene oxide. The peaked distribution of the homologs is indicated by their higher concentration (weight %) at the middle of the distribution range. As is shown in FIG. 3, the most prevalent EO adduct is 4 in both processes even though 6 EO is added. The degree of peaking is 58 for C/16S and 49 for C/16.

Example 3

Compatibility of Ethoxylated Alkylamine with Potassium Glyphosate

Compatibility of cocoamine-5EO (C/15), cocoamine-6EO (C/16), and tallowamine-10EO (T/20) by the new BF3-catalyzed process (the "S" process) and by the "N" process were compared with the regular, hydroxide-catalyzed process (the "R" process) in potassium glyphosate solution. Solution Cloud Point was used to compare the solutions. As shown in Table 1, glyphosate formulas containing 10% ethoxylated alkylamine made by the peaked process have higher Cloud Point, indicating that it is more stable than the formula containing the ethoxylated alkylamine made by conventional processes.

Cloud Point Method

A sample of a stable, transparent formulation is first heated in a 90+° C. water bath. As the temperature of the sample increases "cloudiness" is usually observed. Heating is continued until the cloudiness of the solution is maximized, i.e., the polymeric components dissolved in the formulation precipitate out of solution. If the temperature exceeds 90° C. and no cloudiness is apparent, the result is recorded as CP>90° C.

Next, the solution is slowly cooled by removing the formulation sample from the water bath while gently agitating the sample (e.g., by stirring with a thermometer) and monitoring the dissolution of the suspended polymeric material. When the cloud point temperature is reached the transition increases dramatically due to the remixing or dissolution of the precipitated or polymeric phase.

The temperature at which the formulation sample returns to transparency is recorded as the cloud point for that sample. This analysis is repeated on several different samples. The average observed cloud point of these samples is calculated and reported as the cloud point of the particular formulation tested.

TABLE 1

Cloud Point of concentrated glyphosate formula containing ethoxylated alkylmines prepared from the regular and the peaked processes.

| K-glyphosate wt % a.i. | Surfactant wt % | Surfactant Description | CLOUD POINT (° C.) | |
| --- | --- | --- | --- | --- |
| | | | Peaked Process | Comparative "R" Process |
| 54.8 | 10 | Cocoamine-5EO | 66 ("N") | 58 |
| 54.6 | 10 | Cocoamine-6EO | 59 ("S") | RT separate* |
| 54.6 | 10 | Cocoamine-2EO:Tallowamine 10EO = 35:65 (wt./wt. Ratio) | 44 ("S") | RT separate* |
| 40.3 | 10 | Tallowamine-9EO | 75 ("N") | 71 |
| 54.6 | 9 | Cocoamine-2EO:Tallowamine 9EO = 35:65 (wt./wt. Ratio) | 58 ("N") | 52 |

*RT—room temperature (at room temperature the surfactant is not sufficient soluble to avoid phase separation)
Water was used to balance the solutions to 100 wt %.

Example 4

Preparation of Ethoxylated Coco Amine Using 6 Moles of EO (the "N" Process)

Stage 1: Distilled coco amine (520 g, 2.6 moles) was charged to a one-gallon stainless steel pressure vessel and then heated at 130° C. under nitrogen purging for 30 minutes to reduce its moisture content to less than 0.1%. Ethylene Oxide (230 g, 5.23 moles) was then added to the pressure vessel over a period of 40 minutes while the temperature was maintained at 150-160° C. Following a 30-minute period of digestion, the reaction mixture sampled and analyzed. Its Total Amine Value is 194 mg KOH/g, indicating that the 2.00 moles of ethylene oxide has been consumed for the ethoxylation of 1 mole of coco amine.

Stage 2: The product mixture was then cooled to 115° C. Ethylene oxide (320 g, 7.27 moles) was then added to the pressure vessel over a period 50 minutes, while the temperature was maintained at 115-125° C. Following a 60-minute period of digestion, the reaction mixture was purged with nitrogen, then samples and analyzed. Its Total Amine Value is 138 mg KOH/g, indicating that in this stage, 2.7 moles of ethylene oxide has been consumed for the ethoxylation of 1 mole of coco amine.

Stage 3: Potassium hydroxide (2.50 g, 0.02 moles) was charged to the pressure vessel. The reaction mixture was purged with nitrogen, then heated at 150° C. for 30 minutes under nitrogen purging to reduce its moisture content to less than 0.1%.

Ethylene Oxide (150 g, 3.4 moles) was then added to the pressure vessel over a period of 20 minutes while the temperature was maintained at 150-160° C. Following a 30-minute period of digestion, the reaction mixture was purge with nitrogen to remove the trace of unreacted ethylene oxide, then cooled to 50° C. and discharged. Its TAV is 120 mg KOH/g, indicating that a total of 6.1 moles of ethylene oxide have been consumed for the ethoxylation each mole of coco amine. The content of dioxane (about 150 ppm) and EGDs (about 2.5%) of the final product are much lower than the content of dioxane (about 5000 ppm) and EGDs (about 7.5%) of its counterpart made by the acid-catalyzed process.

Figure 4:
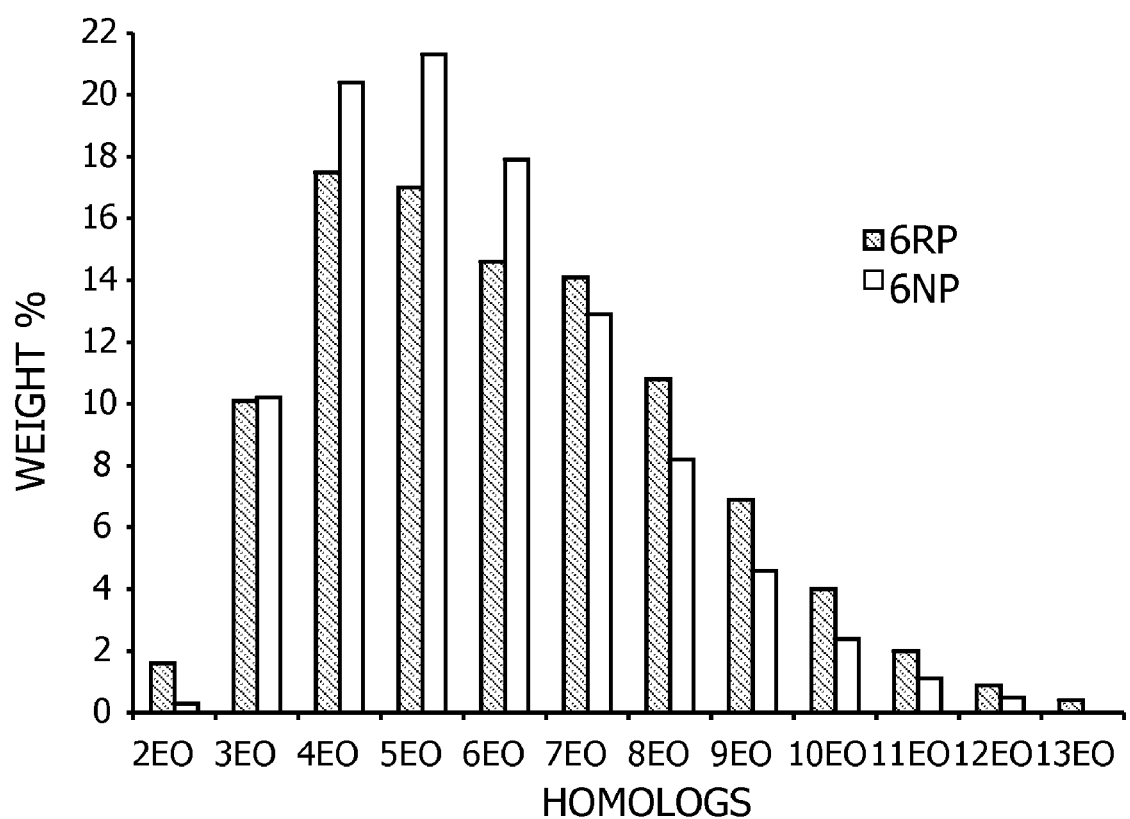
FIG. 4: Homolog distribution of the 6-mole EO adduct of coco amine prepared by the regular ethoxylation process (6RP) and the new ethoxylation process (6NP). The degree of peaking is 60 for 6NP and 49 for 6RP.

FIG. 4 illustrates the homologs distribution of the resulting ethoxylated product (6NP) and of its counterpart that is prepared by the regular, hydroxide-catalyzed ethoxylation of the coco amine with the same number of moles (6) of the ethylene oxide (6RP) that has the same Total Amine Value. The degree of peaking is 60 for 6NP and 49 for 6RP, indicating that the 6NP product made by the new process possesses a peaked ethoxylation distribution.

Example 5

Preparation of Ethoxylated Coco Amine by the "N" Process Using 8 Moles of Ethylene Oxide Stage 1: Distilled coco amine (520 g, 2.6 moles) was charged to a one-gallon stainless steel pressure vessel and then heated at 130° C. under nitrogen purging for 30 minutes to reduce its moisture content to less than 0.1%. Ethylene Oxide (230 g, 5.23 moles) was then added to the pressure vessel over a period of 40 minutes while the temperature was maintained at 150-160° C. Following a 30-minute period of digestion, the reaction mixture sampled and analyzed. Its Total Amine Value is 194 mg KOH/g, indicating that the 2.00 moles of ethylene oxide has been consumed for the ethoxylation of 1 mole of coco amine.

Stage 2: The product mixture was then cooled to 115° C. Ethylene oxide (460 g, 10.46 moles) was then added to the pressure vessel over a period 75 minutes, while the temperature was maintained at 115-125° C. Following a 60-minute period of digestion, the reaction mixture was purged with nitrogen, then samples and analyzed. Its Total Amine Value is 122 mg KOH/g, indicating that in this stage, 3.9 moles of ethylene oxide has been consumed for the ethoxylation of 1 mole of coco amine.

Stage 3: Potassium hydroxide (3.0 g, 0.025 moles) was charged to the pressure vessel. The reaction mixture was purged with nitrogen, then heated at 150° C. for 30 minutes under nitrogen purging to reduce its moisture content to less than 0.1%. Ethylene Oxide (465 g, 6.02 moles) was then added to the pressure vessel over a period of 20 minutes while the temperature was maintained at 150-160° C. Following a 30-minute period of digestion, the reaction mixture was purge with nitrogen to remove the trace of unreacted ethylene oxide, then cooled to 50° C. and discharged. Its TAV is 101 mg KOH/g, indicating that a total of 8.08 moles of ethylene oxide have been consumed for the ethoxylation each mole of coco amine. The content of dioxane (about 200 ppm) and EGDs (about 2.7%) of the final product are much lower than the content of dioxane (about 8000 ppm) and EGDs (about 9.0%) made by the acid-catalyzed process.

Figure 5:
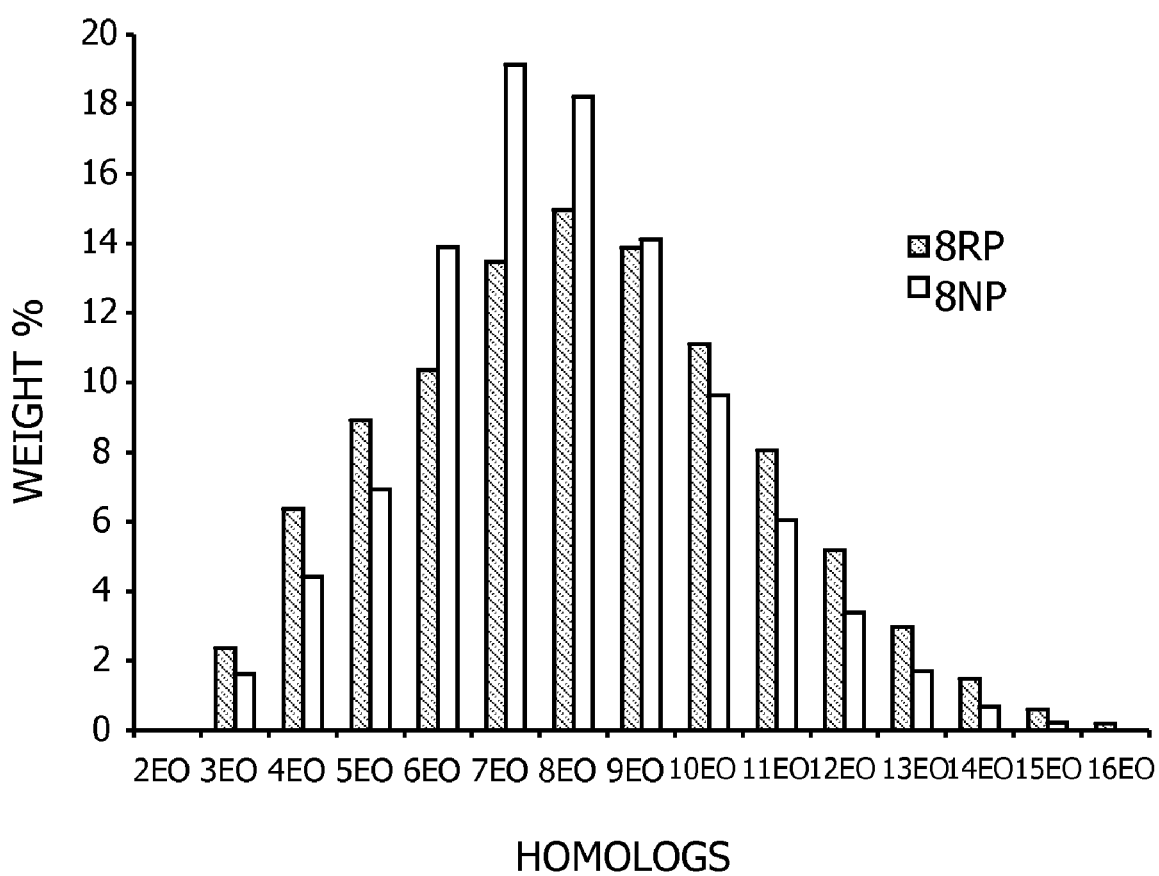
FIG. 5: Homolog distribution of 8-mole EO adduct of coco amine prepared by the regular ethoxylation process (8RP) and the new ethoxylation process (8NP). The degree of peaking is 51 for 8NP and 42 for 8RP.

FIG. 5 illustrates the homologs distribution of the resulting ethoxylated product (8NP) and of its counterpart that is prepared by the regular, hydroxide-catalyzed ethoxylation of the coco amine with the same number of moles (8) of the ethylene oxide (8RP). The degree of peaking is 51 for 8NP and 42 for 8RP, indicating that the 8NP product made by the new process possesses a peaked ethoxylation distribution.

Example 6

Preparation of Ethoxylated Coco Amine Using 9 Moles of Ethylene Oxide

In this experiment, the Stage 1 Ethoxylation (non-catalyzed reaction of coco amine with 2 moles of ethylene oxide) was by-passed. Instead, the commercially available Ethomeen C/12, having a Total Amine Value of 195 mg KOH/g, was used as the starting material.

Stage 2: Ethomeen C/12 (700 g, 2.43 moles) containing less than 0.1% water was charged to a one-gallon stainless steel pressure vessel, purged with nitrogen then heated to 115° C. Ethylene oxide (450 g, 10.22 moles) was then added to the pressure vessel over a period 75 minutes, while the temperature was maintained at 115-125° C. Following a 60-minute period of digestion, the reaction mixture was purged with nitrogen, then samples and analyzed. Its Total Amine Value is 120 mg KOH/g, indicating that in this stage, 4.1 moles of ethylene oxide has been consumed for the ethoxylation of 1 mole of coco amine.

Stage 3: Potassium hydroxide (3.7 g, 0.03 moles) was charged to the pressure vessel. The reaction mixture was purged with nitrogen, then heated at 150° C. for 30 minutes under nitrogen purging to reduce its moisture content to less than 0.1%. Ethylene Oxide (330 g, 7.50 moles) was then added to the pressure vessel over a period of 20 minutes while the temperature was maintained at 140-150° C. Following a 30-minute period of digestion, the reaction mixture was purge with nitrogen to remove the trace of unreacted ethylene oxide, then cooled to 50° C. and discharged. Its TAV is 93 mg KOH/g, indicating that total of 9.2 moles of ethylene oxide have been consumed for the ethoxylation each mole of coco amine in this preparation. The content of dioxane (about 200 ppm) and EGDs (about 3.0%) of the final product are much lower than the content of dioxane (about 12000 ppm) and EGDs (about 11.0%) of its counterpart made by the acid-catalyzed process.

Figure 6:
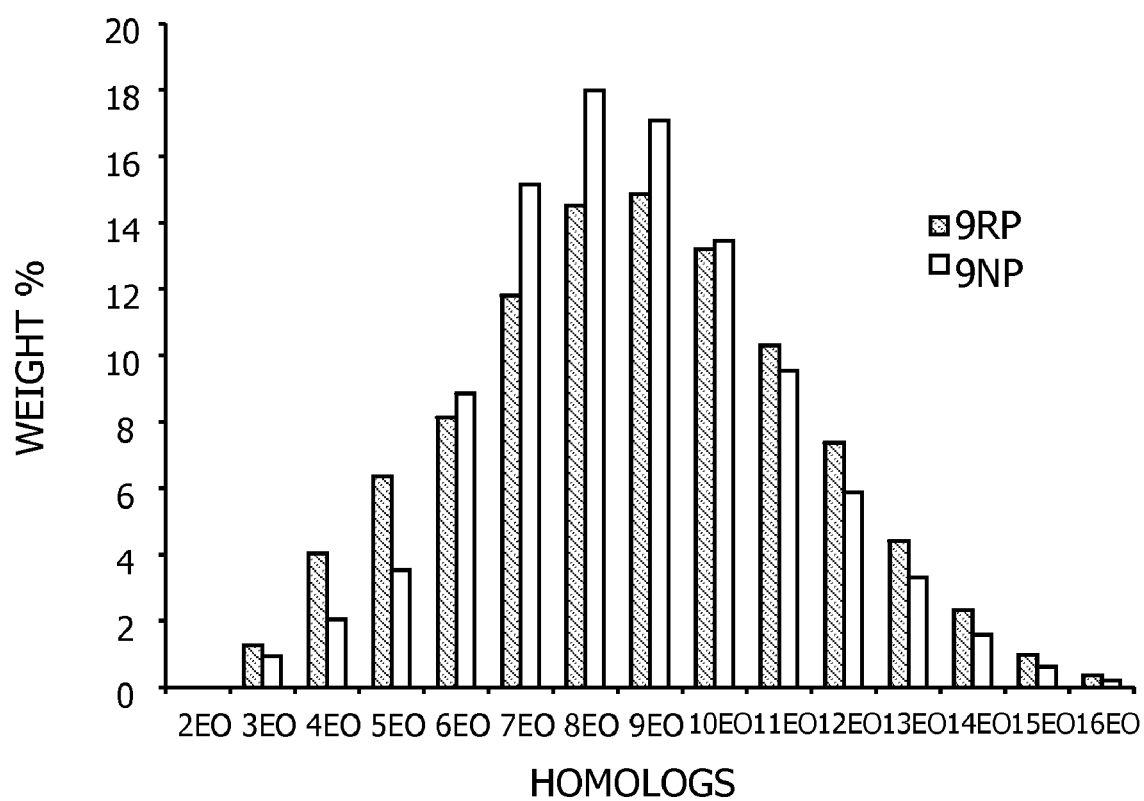
FIG. 6: Homolog distribution of 9-mole EO adduct of coco amine prepared by regular ethoxylation process (9RP) and new ethoxylation process (9NP). The degree of peaking is 50 for 9NP and 43 for 9RP.
Figure 7:
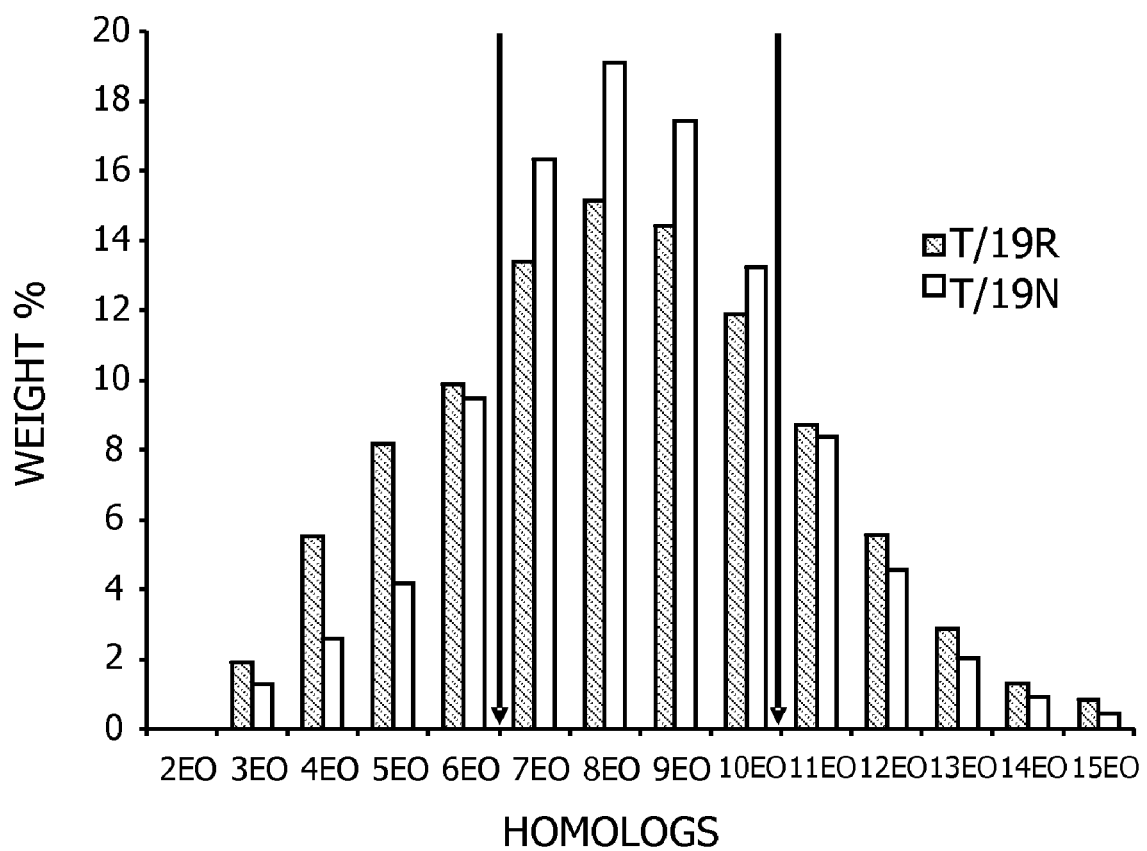
FIG. 7: Homolog distribution of 9-mole EO adduct of tallowamine prepared by regular ethoxylation process (9R) and new "N" ethoxylation process (9N). The degree of peaking is 53 for T/19N and 43 for T/19R.

FIG. 6 illustrates the homologs distribution of the resulting ethoxylated product (9NP) and of its counterpart that is prepared by the regular, hydroxide-catalyzed ethoxylation of the coco amine with the same number of moles (9) of the ethylene oxide (9RP). The degree of peaking is 50 for 9NP and 43 for 9RP, indicating that the 9NP product made by the new process according possesses a peaked ethoxylation distribution.

Example 7

Effect of Reduction of Higher EO Adduct on the Cloud Point of Glyphosate Formulations Adding 0.2% of PEG-600 (~13.6EO) into a 62% K-glyphosate solution resulted in a hazy product. However, adding ~25% diethylene glycol (2EO) into the same K-glyphosate solution resulted in a clear solution. This shows that, in concentrated glyphosate solutions, a higher EO adduct has a much stronger adverse effect on the cloud point than a lower EO adduct. Therefore, even a slight reduction in concentration of the higher EO adduct could improve the cloud point of glyphosate formulation dramatically. This has been demonstrated in example 3.

Example 8

Homolog Distribution of 9-Mole EO Adduct of Tallowamine Prepared by the "R" Ethoxylation Process and the "N" Ethoxylation Process of the Present Invention Product T/19N was produced using a very similar process as outlined in example 6. General conditions have been also listed in Table A. The final Total Amine value is 1.50 for T/19N and 1.51 for T/19R.

The invention claimed is:

1. A stable herbicidal formulation which comprises at least one herbicidally active compound and at least one adjuvant surfactant, wherein said surfactant comprises an ethoxylated alkyl(ether)amine with peaked distribution, said ethoxylated alkyl(ether)amine with peaked distribution characterized by a degree of peaking that is at least 5% higher than that of the conventional non-peaked ethoxylated alkyl(ether)amines having the same carbon-chain length and average EO chain length prepared via conventional base catalysis, wherein conventional base catalysis comprises NaOH-catalyzed reaction of $RNH_2$ with alkylene oxide conducted entirely under autogenous pressure up to 90 psig (621 kPa) at a catalyst concentration of 0.2 wt. % and a temperature between 160° and 180° C.

2. The formulation of claim 1 wherein said peaked distribution is defined by a degree of peaking at least 7% greater than that of conventional ethoxylated alkyl(ether)amines having the same carbon-chain length and average EO chain length prepared via conventional base catalysis.

3. The formulation of claim 2 wherein said peaked distribution is defined by a degree of peaking at least 10% greater than that of a conventional ethoxylated alkyl(ether)amines having the same carbon-chain length and average EO chain length prepared via conventional base catalysis.

4. The formulation of claim 1 wherein said herbicidally active compound is a glyphosate salt.

5. The formulation of claim 4 wherein the glyphosate salt is selected from the group consisting of Na, K, $NH_4$, IPA, MEA, DEA, TEA, TMS and mixtures thereof.

6. The formulation of claim 4 wherein the glyphosate formulation is a stable liquid formulation with a concentration of glyphosate in the range of 360-600 g ae/l.

7. The formulation of claim 4 wherein the ratio of glyphosate (wt % ae) to the peaked distribution ethoxylated alkyl (ether)amine surfactant is between 2:1 and 25:1.

8. The formulation of claim 1 further comprising a co-herbicide selected from the group consisting of acifluorfen, asulam, benazolin, bentazon, bialaphos, bromacil, bromoxynil, chloramben, clopyralid, 2,4-D, 2,4-DB, pelargonic acid, dalapon, dicamba, dichlorprop, diclofop, endothall, fenac, fenoxaprop, flamprop, fluazifop, fluoroglycofen, fomesafen, fosamine, glufosinate, haloxyfop, imazameth, imazamethabenz, imazamox, imazapyr, imazaquin, imazethapyr, ioxynil, MCPA, MCPB, mecoprop, methylarsonic acid, naptalam, nonanoic acid, picloram, sulfamic acid, 2,3,6-TBA, TCA, triclopyr, salts thereof, and mixtures thereof.

9. The formulation of claim 1 wherein said at least one ethoxylated alkyl(ether)amine with peaked distribution is of formula (III)

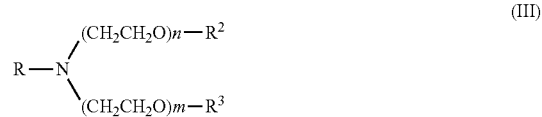

wherein R selected from a linear or branched, saturated or non-saturated alkyl group containing 8-22 carbon atoms, or a group of the formula: R'-0-(A)x-(B)y-(C)z-, wherein A and B are polyalkylene oxide groups, C is methylene group, R' is a linear or branched, saturated or non-saturated alkyl group containing 8-22 carbon atoms, x, y and z vary from 0 to 5, and n and m varies from 1-15, and each of $R^2$ and $R^3$ is independently selected from H, methyl or ethyl, wherein said ethoxylated alkyl(ether)amine with peaked distribution possesses a degree of peaking that is at least 5% higher than that of the conventional non-peaked ethoxylated alkyl(ether)amines having the same carbon-chain length and average EO chain length prepared via conventional base catalysis.

10. The formulation of claim 9 wherein said alkyl groups are derived from tallow, coconut oil, soybean oil, palm oil, and palm kernel oil.

11. The formulation of claim 9 wherein the total number of moles (n+m) is from 3-15.

12. The formulation of claim 9 wherein the ethoxylated alkyl(ether)amine with peaked distribution is derived from cocoamine, tallowamine, soya amine, oleyl amine, and palm amine.

13. The formulation of claim 9 wherein said ethoxylated alkyl(ether)amine is selected from the group consisting of an ethoxylated tallowamine with 4 to 15 moles of EO, ethoxylated cocoamine with 4 to 15 moles of EO, ethoxylated alkylamine with 4 to 15 moles of EO and mixtures thereof.

* * * * *